United States Patent
Razzaque et al.

(10) Patent No.: US 9,949,700 B2
(45) Date of Patent: Apr. 24, 2018

(54) MEDICAL DEVICE APPROACHES

(71) Applicant: InnerOptic Technology, Inc., Hillsborough, NC (US)

(72) Inventors: Sharif Razzaque, Boulder, CO (US); Luv Kohli, Durham, NC (US); Andrei State, Chapel Hill, NC (US)

(73) Assignee: InnerOptic Technology, Inc., Hillsborough, NC (US)

( * ) Notice: Subject to any disclaimer, the term of this patent is extended or adjusted under 35 U.S.C. 154(b) by 103 days.

(21) Appl. No.: 15/199,711

(22) Filed: Jun. 30, 2016

(65) Prior Publication Data

US 2017/0024903 A1    Jan. 26, 2017

Related U.S. Application Data

(60) Provisional application No. 62/195,676, filed on Jul. 22, 2015.

(51) Int. Cl.
*G06K 9/00* (2006.01)
*A61B 6/03* (2006.01)
(Continued)

(52) U.S. Cl.
CPC ............ *A61B 6/037* (2013.01); *A61B 6/12* (2013.01); *A61B 6/461* (2013.01); *A61B 6/463* (2013.01);
(Continued)

(58) Field of Classification Search
None
See application file for complete search history.

(56) References Cited

U.S. PATENT DOCUMENTS

| 3,556,079 A | 1/1971 | Omizo |
| 4,058,114 A | 11/1977 | Soldner |

(Continued)

FOREIGN PATENT DOCUMENTS

| EP | 0 427 358 | 5/1991 |
| JP | S63-290550 A | 11/1988 |

(Continued)

OTHER PUBLICATIONS

U.S. Appl. No. 11/828,826 including its ongoing prosecution history, including without limitation Office Actions, Amendments, Remarks, and any other potentially relevant documents, Jul. 26, 2007, Keller et al.

(Continued)

*Primary Examiner* — Shervin Nakhjavan
(74) *Attorney, Agent, or Firm* — Knobbe, Martens, Olson & Bear, LLP

(57) ABSTRACT

A system and method for providing image guidance for planning approach paths for one or more medical devices at a target location. The system can receive a volumetric medical image, determine a density of content within the volumetric medical image, receive an indication of a target location within the volumetric medical image, identify obstructing objects within the volumetric medical image, and determine a plurality of pathways from an approach region of the volumetric medical image to the target location. The system can cause a display to concurrently display the volumetric medical image and a plurality of emplacements for one or more medical imaging devices.

18 Claims, 6 Drawing Sheets

(51) Int. Cl.

| | | |
|---|---|---|
| *A61B 6/12* | (2006.01) | |
| *A61B 6/00* | (2006.01) | |
| *G06T 19/00* | (2011.01) | |
| *G06T 7/11* | (2017.01) | |
| *G06T 7/136* | (2017.01) | |
| *A61B 5/055* | (2006.01) | |
| *A61B 34/10* | (2016.01) | |
| *A61B 34/20* | (2016.01) | |
| *A61B 90/00* | (2016.01) | |

(52) U.S. Cl.
CPC .............. *A61B 6/5247* (2013.01); *G06T 7/11* (2017.01); *G06T 7/136* (2017.01); *G06T 19/003* (2013.01); *A61B 5/055* (2013.01); *A61B 6/032* (2013.01); *A61B 2034/107* (2016.02); *A61B 2034/2065* (2016.02); *A61B 2090/378* (2016.02); *G06T 2207/10072* (2013.01)

(56) References Cited

U.S. PATENT DOCUMENTS

| | | |
|---|---|---|
| RE30,397 E | 9/1980 | King |
| 4,249,539 A | 2/1981 | Vilkomerson et al. |
| 4,294,544 A | 10/1981 | Altschuler et al. |
| 4,390,025 A | 6/1983 | Takemura et al. |
| 4,407,294 A | 10/1983 | Vilkomerso |
| 4,431,006 A | 2/1984 | Trimmer et al. |
| 4,567,896 A | 2/1986 | Barnea et al. |
| 4,583,538 A | 4/1986 | Onik et al. |
| 4,620,546 A | 11/1986 | Aida et al. |
| 4,671,292 A | 6/1987 | Matzuk |
| 4,839,836 A | 6/1989 | Fonsalas |
| 4,862,873 A | 9/1989 | Yajima et al. |
| 4,884,219 A | 11/1989 | Waldren |
| 4,899,756 A | 2/1990 | Sonek |
| 4,911,173 A | 3/1990 | Terwilliger |
| 4,945,305 A | 7/1990 | Blood |
| 5,076,279 A | 12/1991 | Arenson et al. |
| 5,078,140 A | 1/1992 | Kwoh |
| 5,078,142 A | 1/1992 | Siczek et al. |
| 5,095,910 A | 3/1992 | Powers |
| 5,109,276 A | 4/1992 | Nudelman et al. |
| 5,158,088 A | 10/1992 | Nelson et al. |
| 5,161,536 A | 11/1992 | Vikomerson et al. |
| 5,193,120 A | 3/1993 | Gamache et al. |
| 5,209,235 A | 5/1993 | Brisken et al. |
| 5,249,581 A | 10/1993 | Horbal et al. |
| 5,251,127 A | 10/1993 | Raab |
| 5,261,404 A | 11/1993 | Mick et al. |
| 5,265,610 A | 11/1993 | Darrow et al. |
| 5,271,400 A | 12/1993 | Dumoulin et al. |
| 5,307,153 A | 4/1994 | Maruyama et al. |
| 5,309,913 A | 5/1994 | Kormos et al. |
| 5,323,002 A | 6/1994 | Sampsell et al. |
| 5,371,543 A | 12/1994 | Anderson |
| 5,383,454 A | 1/1995 | Bucholz |
| 5,394,875 A | 3/1995 | Lewis et al. |
| 5,411,026 A | 5/1995 | Carol |
| 5,433,198 A | 7/1995 | Desai |
| 5,433,739 A | 7/1995 | Sluijter |
| 5,443,489 A | 8/1995 | Ben-Haim |
| 5,446,798 A | 8/1995 | Morita et al. |
| 5,447,154 A | 9/1995 | Cinquin et al. |
| 5,452,024 A | 9/1995 | Sampsell |
| 5,457,493 A | 10/1995 | Leddy et al. |
| 5,474,073 A | 12/1995 | Schwartz et al. |
| 5,476,096 A | 12/1995 | Olstad et al. |
| 5,483,961 A | 1/1996 | Kelly et al. |
| 5,488,431 A | 1/1996 | Gove et al. |
| 5,489,952 A | 2/1996 | Gove et al. |
| 5,491,510 A | 2/1996 | Gove |
| 5,494,039 A | 2/1996 | Onik et al. |
| 5,503,152 A | 4/1996 | Oakley et al. |
| 5,505,204 A | 4/1996 | Picot et al. |
| 5,515,856 A | 5/1996 | Olstad et al. |
| 5,517,990 A | 5/1996 | Kalfas et al. |
| 5,526,051 A | 6/1996 | Gove et al. |
| 5,526,812 A | 6/1996 | Dumoulin et al. |
| 5,529,070 A | 6/1996 | Augustine et al. |
| 5,531,227 A | 7/1996 | Schneider |
| 5,532,997 A | 7/1996 | Pauli |
| 5,541,723 A | 7/1996 | Tanaka |
| 5,558,091 A | 9/1996 | Acker et al. |
| 5,568,811 A | 10/1996 | Olstad |
| 5,570,135 A | 10/1996 | Gove et al. |
| 5,579,026 A | 11/1996 | Tabata |
| 5,581,271 A | 12/1996 | Kraemer |
| 5,588,948 A | 12/1996 | Takahashi et al. |
| 5,608,468 A | 3/1997 | Gove et al. |
| 5,608,849 A | 3/1997 | King, Jr. |
| 5,611,345 A | 3/1997 | Hibbeln |
| 5,611,353 A | 3/1997 | Dance et al. |
| 5,612,753 A | 3/1997 | Poradish et al. |
| 5,625,408 A | 4/1997 | Matsugu et al. |
| 5,628,327 A | 5/1997 | Unger et al. |
| 5,629,794 A | 5/1997 | Magel et al. |
| 5,630,027 A | 5/1997 | Venkateswar et al. |
| 5,647,361 A | 7/1997 | Damadian |
| 5,647,373 A | 7/1997 | Paltieli et al. |
| 5,660,185 A | 8/1997 | Shmulewitz et al. |
| 5,662,111 A | 9/1997 | Cosman |
| 5,699,444 A | 12/1997 | Palm |
| 5,701,898 A | 12/1997 | Adam et al. |
| 5,701,900 A | 12/1997 | Shehada et al. |
| 5,726,670 A | 3/1998 | Tabata et al. |
| 5,728,044 A | 3/1998 | Shan |
| 5,758,650 A | 6/1998 | Miller et al. |
| 5,766,135 A | 6/1998 | Terwilliger |
| 5,784,098 A | 7/1998 | Shoji et al. |
| 5,792,147 A | 8/1998 | Evans et al. |
| 5,793,701 A | 8/1998 | Wright et al. |
| 5,797,849 A | 8/1998 | Vesely et al. |
| 5,807,395 A | 9/1998 | Mulier et al. |
| 5,810,008 A | 9/1998 | Dekel et al. |
| 5,817,022 A | 10/1998 | Vesely |
| 5,820,554 A | 10/1998 | Davis et al. |
| 5,820,561 A | 10/1998 | Olstad et al. |
| 5,829,439 A | 11/1998 | Yokosawa et al. |
| 5,829,444 A | 11/1998 | Ferre et al. |
| 5,851,183 A | 12/1998 | Bodiolz |
| 5,870,136 A | 2/1999 | Fuchs et al. |
| 5,891,034 A | 4/1999 | Bucholz |
| 5,920,395 A | 7/1999 | Schulz |
| 5,961,527 A | 10/1999 | Whitmore, III et al. |
| 5,967,980 A | 10/1999 | Ferre et al. |
| 5,991,085 A | 11/1999 | Rallison et al. |
| 6,016,439 A | 1/2000 | Acker |
| 6,019,724 A | 2/2000 | Gronningsaeter et al. |
| 6,048,312 A | 4/2000 | Ishrak et al. |
| 6,064,749 A | 5/2000 | Hirota et al. |
| 6,091,546 A | 7/2000 | Spitzer |
| 6,095,982 A | 8/2000 | Richards-Kortum et al. |
| 6,099,471 A | 8/2000 | Torp et al. |
| 6,108,130 A | 8/2000 | Raj |
| 6,122,538 A | 9/2000 | Sliwa, Jr. et al. |
| 6,122,541 A | 9/2000 | Cosman et al. |
| 6,160,666 A | 12/2000 | Rallison et al. |
| 6,167,296 A | 12/2000 | Shahidi |
| 6,181,371 B1 | 1/2001 | Maguire, Jr. |
| RE37,088 E | 3/2001 | Olstad et al. |
| 6,216,029 B1 | 4/2001 | Paltieli |
| 6,241,725 B1 | 6/2001 | Cosman |
| 6,245,017 B1 | 6/2001 | Hashimoto et al. |
| 6,246,898 B1 | 6/2001 | Vesely et al. |
| 6,248,101 B1 | 6/2001 | Witmore, III et al. |
| 6,261,234 B1 | 7/2001 | Lin |
| 6,341,016 B1 | 1/2002 | Malione |
| 6,348,058 B1 | 2/2002 | Melkent et al. |
| 6,350,238 B1 | 2/2002 | Olstad et al. |
| 6,352,507 B1 | 3/2002 | Torp et al. |
| 6,379,302 B1 | 4/2002 | Kessman et al. |
| 6,385,475 B1 | 5/2002 | Cinquin et al. |

(56) References Cited

U.S. PATENT DOCUMENTS

| | | |
|---|---|---|
| 6,442,417 B1 | 8/2002 | Shahidi et al. |
| 6,447,450 B1 | 9/2002 | Olsdat |
| 6,456,868 B2 | 9/2002 | Saito et al. |
| 6,470,207 B1 | 10/2002 | Simon et al. |
| 6,471,366 B1 | 10/2002 | Hughson et al. |
| 6,477,400 B1 | 11/2002 | Barrick |
| 6,478,793 B1 | 11/2002 | Cosman et al. |
| 6,503,195 B1 | 1/2003 | Keller et al. |
| 6,511,418 B2 | 1/2003 | Shahidi et al. |
| 6,517,485 B2 | 2/2003 | Torp et al. |
| 6,518,939 B1 | 2/2003 | Kikuchi |
| 6,527,443 B1 | 3/2003 | Vilsmeier |
| 6,529,758 B2 | 3/2003 | Shahidi |
| 6,537,217 B1 | 3/2003 | Steinar et al. |
| 6,545,706 B1 | 4/2003 | Edwards et al. |
| 6,546,279 B1 | 4/2003 | Bova et al. |
| 6,551,325 B2 | 4/2003 | Neubauer et al. |
| 6,570,566 B1 | 5/2003 | Yoshigahara |
| 6,575,969 B1 | 6/2003 | Rittman, III et al. |
| 6,579,240 B2 | 6/2003 | Bjaerum et al. |
| 6,587,711 B1 | 7/2003 | Alfano et al. |
| 6,591,130 B2 | 7/2003 | Shahidi |
| 6,592,522 B2 | 7/2003 | Bjaerum et al. |
| 6,594,517 B1 | 7/2003 | Nevo |
| 6,597,818 B2 | 7/2003 | Kumar et al. |
| 6,604,404 B2 | 8/2003 | Paltieli et al. |
| 6,616,610 B2 | 9/2003 | Steininger et al. |
| 6,626,832 B1 | 9/2003 | Paltieli et al. |
| 6,652,462 B2 | 11/2003 | Bjaerum et al. |
| 6,669,635 B2 | 12/2003 | Kessman et al. |
| 6,676,599 B2 | 1/2004 | Torp et al. |
| 6,689,067 B2 | 2/2004 | Sauer et al. |
| 6,695,786 B2 | 2/2004 | Wang et al. |
| 6,711,429 B1 | 3/2004 | Gilboa et al. |
| 6,725,082 B2 | 4/2004 | Sati et al. |
| 6,733,458 B1 | 5/2004 | Steins et al. |
| 6,764,449 B2 | 7/2004 | Lee et al. |
| 6,766,184 B2 | 7/2004 | Utzinger et al. |
| 6,768,496 B2 | 7/2004 | Bieger et al. |
| 6,775,404 B1 | 8/2004 | Pagoulatos et al. |
| 6,782,287 B2 | 8/2004 | Grzeszczuk et al. |
| 6,783,524 B2 | 8/2004 | Anderson et al. |
| 6,827,723 B2 | 12/2004 | Carson |
| 6,863,655 B2 | 3/2005 | Bjaerum et al. |
| 6,873,867 B2 | 3/2005 | Vilsmeier |
| 6,875,179 B2 | 4/2005 | Ferguson et al. |
| 6,881,214 B2 | 4/2005 | Cosman et al. |
| 6,895,268 B1 | 5/2005 | Rahn et al. |
| 6,915,150 B2 | 7/2005 | Cinquin et al. |
| 6,917,827 B2 | 7/2005 | Kienzle, III |
| 6,923,817 B2 | 8/2005 | Carson et al. |
| 6,936,048 B2 | 8/2005 | Hurst |
| 6,947,783 B2 | 9/2005 | Immerz |
| 6,968,224 B2 | 11/2005 | Kessman et al. |
| 6,978,167 B2 | 12/2005 | Dekel et al. |
| 7,008,373 B2 | 3/2006 | Stoianovici et al. |
| 7,033,360 B2 | 4/2006 | Cinquin et al. |
| 7,072,707 B2 | 7/2006 | Galloway, Jr. et al. |
| 7,077,807 B2 | 7/2006 | Torp et al. |
| 7,093,012 B2 | 8/2006 | Oltad et al. |
| 7,110,013 B2 | 9/2006 | Ebersole et al. |
| 7,171,255 B2 | 1/2007 | Holupka et al. |
| 7,209,776 B2 | 4/2007 | Leitner |
| 7,245,746 B2 | 7/2007 | Bjaerum et al. |
| 7,248,232 B1 | 7/2007 | Yamazaki et al. |
| 7,261,694 B2 | 8/2007 | Torp et al. |
| 7,313,430 B2 | 12/2007 | Urquhart et al. |
| 7,331,932 B2 | 2/2008 | Leitner |
| 7,351,205 B2 | 4/2008 | Szczech et al. |
| 7,379,769 B2 | 5/2008 | Piron et al. |
| 7,385,708 B2 | 6/2008 | Ackerman et al. |
| 7,392,076 B2 | 6/2008 | Moctezuma de la Barrera |
| 7,398,116 B2 | 7/2008 | Edwards |
| 7,466,303 B2 | 12/2008 | Yi et al. |
| 7,480,533 B2 | 1/2009 | Cosman et al. |
| 7,505,809 B2 | 3/2009 | Strommer et al. |
| 7,588,541 B2 | 9/2009 | Floyd et al. |
| 7,596,267 B2 * | 9/2009 | Accomazzi ............ G06K 9/346 382/173 |
| 7,652,259 B2 | 1/2010 | Kimchy et al. |
| 7,662,128 B2 | 2/2010 | Salcudean et al. |
| 7,678,052 B2 | 3/2010 | Torp et al. |
| 7,728,868 B2 | 6/2010 | Razzaque et al. |
| 7,747,305 B2 * | 6/2010 | Dean .................. A61F 2/30942 345/420 |
| 7,797,032 B2 | 9/2010 | Martinelli et al. |
| 7,798,965 B2 | 9/2010 | Torp et al. |
| 7,833,168 B2 | 11/2010 | Taylor et al. |
| 7,833,221 B2 | 11/2010 | Voegele et al. |
| 7,846,103 B2 | 12/2010 | Cannon, Jr. et al. |
| 7,876,942 B2 | 1/2011 | Gilboa |
| 7,889,905 B2 | 2/2011 | Higgins et al. |
| 7,912,849 B2 | 3/2011 | Ohrn et al. |
| 7,920,909 B2 | 4/2011 | Lyon et al. |
| 7,962,193 B2 | 6/2011 | Edwards et al. |
| 7,976,469 B2 | 7/2011 | Bonde et al. |
| 8,023,712 B2 | 9/2011 | Ikuma et al. |
| 8,038,631 B1 | 10/2011 | Sanghvi et al. |
| 8,041,413 B2 | 10/2011 | Barbagli et al. |
| 8,050,736 B2 | 11/2011 | Piron et al. |
| 8,052,636 B2 | 11/2011 | Moll et al. |
| 8,066,644 B2 | 11/2011 | Sarkar et al. |
| 8,073,528 B2 | 12/2011 | Zhao et al. |
| 8,086,298 B2 | 12/2011 | Whitmore, III et al. |
| 8,135,669 B2 | 3/2012 | Olstad et al. |
| 8,137,281 B2 | 3/2012 | Huang et al. |
| 8,147,408 B2 | 4/2012 | Bunce et al. |
| 8,152,724 B2 | 4/2012 | Ridley et al. |
| 8,167,805 B2 | 5/2012 | Emery et al. |
| 8,216,149 B2 | 7/2012 | Oonuki et al. |
| 8,221,322 B2 | 7/2012 | Wang et al. |
| 8,228,028 B2 | 7/2012 | Schneider |
| 8,257,264 B2 | 9/2012 | Park et al. |
| 8,296,797 B2 | 10/2012 | Olstad et al. |
| 8,340,379 B2 | 12/2012 | Razzaque et al. |
| 8,350,902 B2 | 1/2013 | Razzaque et al. |
| 8,482,606 B2 | 7/2013 | Razzaque et al. |
| 8,554,307 B2 | 10/2013 | Razzaque et al. |
| 8,585,598 B2 | 11/2013 | Razzaque et al. |
| 8,641,621 B2 | 2/2014 | Razzaque et al. |
| 8,670,816 B2 | 3/2014 | Green et al. |
| 8,690,776 B2 | 4/2014 | Razzaque et al. |
| 8,831,310 B2 | 9/2014 | Razzaque et al. |
| 9,107,698 B2 | 8/2015 | Razzaque et al. |
| 9,282,947 B2 | 3/2016 | Razzaque et al. |
| 9,364,294 B2 | 6/2016 | Razzaque et al. |
| 9,398,936 B2 | 7/2016 | Razzaque et al. |
| 2001/0007919 A1 | 7/2001 | Shahidi |
| 2001/0016804 A1 | 8/2001 | Cunningham et al. |
| 2001/0041838 A1 | 11/2001 | Holupka et al. |
| 2001/0045979 A1 | 11/2001 | Matsumoto et al. |
| 2002/0010384 A1 | 1/2002 | Shahidi et al. |
| 2002/0032772 A1 | 3/2002 | Olstad et al. |
| 2002/0049375 A1 | 4/2002 | Strommer et al. |
| 2002/0077540 A1 | 6/2002 | Kienzie, III |
| 2002/0077543 A1 | 6/2002 | Grzeszczuk et al. |
| 2002/0105484 A1 | 8/2002 | Navab et al. |
| 2002/0135673 A1 | 9/2002 | Favalora et al. |
| 2002/0138008 A1 | 9/2002 | Tsujita et al. |
| 2002/0140814 A1 | 10/2002 | Cohen-Solal et al. |
| 2002/0156375 A1 | 10/2002 | Kessmam et al. |
| 2002/0198451 A1 | 12/2002 | Carson |
| 2003/0040743 A1 | 2/2003 | Cosman et al. |
| 2003/0073901 A1 | 4/2003 | Simon et al. |
| 2003/0135119 A1 | 7/2003 | Lee et al. |
| 2003/0163142 A1 | 8/2003 | Paltieli et al. |
| 2003/0164172 A1 | 9/2003 | Chumas et al. |
| 2003/0231789 A1 | 12/2003 | Willis et al. |
| 2004/0034313 A1 | 2/2004 | Leitner |
| 2004/0078036 A1 | 4/2004 | Keidar |
| 2004/0095507 A1 | 5/2004 | Bishop et al. |
| 2004/0116810 A1 | 6/2004 | Olstad |
| 2004/0147920 A1 | 7/2004 | Keidar |
| 2004/0152970 A1 | 8/2004 | Hunter et al. |

(56) References Cited

U.S. PATENT DOCUMENTS

| | | |
|---|---|---|
| 2004/0181144 A1 | 9/2004 | Cinquin et al. |
| 2004/0215071 A1 | 10/2004 | Frank et al. |
| 2004/0238732 A1 | 12/2004 | State et al. |
| 2004/0243146 A1 | 12/2004 | Chesbrough et al. |
| 2004/0243148 A1 | 12/2004 | Wasielewski |
| 2004/0249281 A1 | 12/2004 | Olstad |
| 2004/0249282 A1 | 12/2004 | Olstad |
| 2004/0254454 A1 | 12/2004 | Kockro |
| 2005/0010098 A1 | 1/2005 | Frigstad et al. |
| 2005/0085717 A1 | 4/2005 | Shahidi |
| 2005/0085718 A1 | 4/2005 | Shahidi |
| 2005/0090742 A1 | 4/2005 | Mine et al. |
| 2005/0107679 A1* | 5/2005 | Geiger .................. G06T 19/003 600/407 |
| 2005/0111733 A1 | 5/2005 | Fors et al. |
| 2005/0159641 A1 | 7/2005 | Kanai |
| 2005/0182316 A1 | 8/2005 | Burdette et al. |
| 2005/0192564 A1 | 9/2005 | Cosman et al. |
| 2005/0219552 A1 | 10/2005 | Ackerman et al. |
| 2005/0222574 A1 | 10/2005 | Giordano et al. |
| 2005/0251148 A1 | 11/2005 | Friedrich |
| 2006/0004275 A1 | 1/2006 | Vija et al. |
| 2006/0020204 A1 | 1/2006 | Serra et al. |
| 2006/0036162 A1 | 2/2006 | Shahidi et al. |
| 2006/0052792 A1 | 3/2006 | Boettiger et al. |
| 2006/0058609 A1 | 3/2006 | Olstad |
| 2006/0058610 A1 | 3/2006 | Olstad |
| 2006/0058674 A1 | 3/2006 | Olstad |
| 2006/0058675 A1 | 3/2006 | Olstad |
| 2006/0100505 A1 | 5/2006 | Viswanathan |
| 2006/0122495 A1 | 6/2006 | Kienzle |
| 2006/0184040 A1 | 8/2006 | Keller et al. |
| 2006/0193504 A1 | 8/2006 | Salgo et al. |
| 2006/0229594 A1 | 10/2006 | Francischelli et al. |
| 2006/0235290 A1 | 10/2006 | Gabriel et al. |
| 2006/0235538 A1 | 10/2006 | Rochetin et al. |
| 2006/0241450 A1 | 10/2006 | Da Silva et al. |
| 2006/0253030 A1 | 11/2006 | Altmann et al. |
| 2006/0253032 A1 | 11/2006 | Altmann et al. |
| 2006/0271056 A1 | 11/2006 | Terrill-Grisoni et al. |
| 2006/0282023 A1 | 12/2006 | Leitner |
| 2006/0293643 A1 | 12/2006 | Wallace et al. |
| 2007/0002582 A1 | 1/2007 | Burwell et al. |
| 2007/0016035 A1 | 1/2007 | Hashimoto |
| 2007/0032906 A1 | 2/2007 | Sutherland et al. |
| 2007/0073155 A1 | 3/2007 | Park et al. |
| 2007/0073455 A1 | 3/2007 | Oyobe et al. |
| 2007/0078346 A1 | 4/2007 | Park et al. |
| 2007/0167699 A1 | 7/2007 | Lathuiliere et al. |
| 2007/0167701 A1 | 7/2007 | Sherman |
| 2007/0167705 A1 | 7/2007 | Chiang et al. |
| 2007/0167771 A1 | 7/2007 | Olstad |
| 2007/0167801 A1 | 7/2007 | Webler et al. |
| 2007/0225553 A1 | 9/2007 | Shahidi |
| 2007/0239281 A1 | 10/2007 | Gotte et al. |
| 2007/0244488 A1 | 10/2007 | Metzger et al. |
| 2007/0255136 A1 | 11/2007 | Kjell et al. |
| 2007/0270718 A1 | 11/2007 | Rochetin et al. |
| 2007/0276234 A1 | 11/2007 | Kristofferson |
| 2008/0004481 A1 | 1/2008 | Bax et al. |
| 2008/0004516 A1 | 1/2008 | DiSilvestro et al. |
| 2008/0030578 A1 | 2/2008 | Razzaque et al. |
| 2008/0039723 A1 | 2/2008 | Suri et al. |
| 2008/0051910 A1 | 2/2008 | Kammerzell et al. |
| 2008/0091106 A1 | 4/2008 | Kim et al. |
| 2008/0114235 A1 | 5/2008 | Unal et al. |
| 2008/0161824 A1 | 7/2008 | McMillen |
| 2008/0200794 A1 | 8/2008 | Teichman et al. |
| 2008/0208031 A1 | 8/2008 | Kurpad et al. |
| 2008/0208081 A1 | 8/2008 | Murphy et al. |
| 2008/0214932 A1 | 9/2008 | Mollard et al. |
| 2008/0232679 A1 | 9/2008 | Hahn et al. |
| 2008/0287794 A1 | 11/2008 | Li et al. |
| 2008/0287805 A1 | 11/2008 | Li |
| 2008/0287837 A1 | 11/2008 | Makin et al. |
| 2009/0024030 A1 | 1/2009 | Lachaine et al. |
| 2009/0118724 A1 | 5/2009 | Zvuloni et al. |
| 2009/0131783 A1 | 5/2009 | Jenkins et al. |
| 2009/0137907 A1 | 5/2009 | Takimoto et al. |
| 2009/0234369 A1 | 9/2009 | Bax et al. |
| 2009/0312629 A1 | 12/2009 | Razzaque et al. |
| 2010/0045783 A1 | 2/2010 | State et al. |
| 2010/0198045 A1 | 8/2010 | Razzaque et al. |
| 2010/0208963 A1 | 8/2010 | Kruecker et al. |
| 2010/0268072 A1 | 10/2010 | Hall et al. |
| 2010/0268085 A1 | 10/2010 | Kruecker et al. |
| 2010/0296718 A1* | 11/2010 | Ostrovsky-Berman ... G06T 7/62 382/133 |
| 2010/0298705 A1 | 11/2010 | Pelissier et al. |
| 2010/0305448 A1 | 12/2010 | Dagonnau et al. |
| 2010/0312121 A1 | 12/2010 | Guan |
| 2010/0331252 A1 | 12/2010 | Clements et al. |
| 2011/0043612 A1 | 2/2011 | Keller et al. |
| 2011/0046483 A1 | 2/2011 | Fuchs et al. |
| 2011/0046486 A1 | 2/2011 | Fuchs et al. |
| 2011/0057930 A1 | 3/2011 | Keller |
| 2011/0082351 A1 | 4/2011 | Razzaque et al. |
| 2011/0201915 A1 | 8/2011 | Gogin et al. |
| 2011/0201976 A1 | 8/2011 | Sanghvi et al. |
| 2011/0230351 A1 | 9/2011 | Fischer et al. |
| 2011/0237947 A1 | 9/2011 | Boctor et al. |
| 2011/0238043 A1 | 9/2011 | Kleven |
| 2011/0251483 A1 | 10/2011 | Razzaque et al. |
| 2011/0274324 A1 | 11/2011 | Clements et al. |
| 2011/0282188 A1 | 11/2011 | Burnside et al. |
| 2011/0288412 A1 | 11/2011 | Deckman et al. |
| 2011/0295108 A1 | 12/2011 | Cox et al. |
| 2011/0301451 A1 | 12/2011 | Rohling |
| 2012/0035473 A1 | 2/2012 | Sanghvi et al. |
| 2012/0059260 A1 | 3/2012 | Robinson |
| 2012/0071759 A1 | 3/2012 | Hagy et al. |
| 2012/0078094 A1 | 3/2012 | Nishina et al. |
| 2012/0108955 A1 | 5/2012 | Razzaque et al. |
| 2012/0143029 A1 | 6/2012 | Silverstein et al. |
| 2012/0143055 A1 | 6/2012 | Cheng et al. |
| 2012/0165679 A1 | 6/2012 | Orome et al. |
| 2012/0259210 A1 | 10/2012 | Harhen et al. |
| 2013/0030286 A1 | 1/2013 | Alouani et al. |
| 2013/0044930 A1 | 2/2013 | Li et al. |
| 2013/0079770 A1 | 3/2013 | Kyle, Jr. et al. |
| 2013/0132374 A1 | 5/2013 | Olstad et al. |
| 2013/0151533 A1 | 6/2013 | Udupa et al. |
| 2013/0178745 A1 | 7/2013 | Kyle et al. |
| 2013/0249787 A1 | 9/2013 | Morimoto |
| 2014/0016848 A1 | 1/2014 | Razzaque et al. |
| 2014/0078138 A1 | 3/2014 | Martin et al. |
| 2014/0180074 A1 | 6/2014 | Green |
| 2014/0201669 A1 | 7/2014 | Liu et al. |
| 2014/0275810 A1 | 9/2014 | Keller et al. |
| 2014/0343404 A1 | 11/2014 | Razzaque et al. |
| 2014/0350390 A1* | 11/2014 | Kudavelly ........... A61B 8/0841 600/424 |
| 2016/0117857 A1 | 4/2016 | State et al. |
| 2016/0166334 A1 | 6/2016 | Razzaque |
| 2016/0166336 A1 | 6/2016 | Razzaque |
| 2016/0196694 A1 | 7/2016 | Lindeman |
| 2017/0065352 A1 | 3/2017 | Razzaque |

FOREIGN PATENT DOCUMENTS

| | | |
|---|---|---|
| JP | H07-116164 A | 5/1995 |
| JP | 2005-058584 | 3/2005 |
| JP | 2005-323669 | 11/2005 |
| JP | 2009-517177 | 4/2009 |
| WO | WO 96/005768 | 2/1996 |
| WO | WO 97/015249 | 5/1997 |
| WO | WO 97/017014 | 5/1997 |
| WO | WO 99/26534 | 6/1999 |
| WO | WO 01/039683 | 6/2001 |
| WO | WO 03/032837 | 4/2003 |
| WO | WO 03/034705 | 4/2003 |
| WO | WO 03/105289 | 12/2003 |
| WO | WO 05/010711 | 2/2005 |
| WO | WO 07/019216 | 2/2007 |

(56) References Cited

FOREIGN PATENT DOCUMENTS

| | | |
|---|---|---|
| WO | WO 07/067323 A2 | 6/2007 |
| WO | WO 07/067323 A3 | 9/2007 |
| WO | WO 08/017051 A2 | 2/2008 |
| WO | WO 09/063423 | 5/2009 |
| WO | WO 09/094646 | 7/2009 |
| WO | WO 10/057315 | 5/2010 |
| WO | WO 10/096419 A2 | 8/2010 |
| WO | WO 11/014687 A2 | 2/2011 |
| WO | WO 12/169990 | 12/2012 |
| WO | WO 13/116240 | 8/2013 |

OTHER PUBLICATIONS

U.S. Appl. No. 15/041,868 including its ongoing prosecution history, including without limitation Office Actions, Amendments, Remarks, and any other potentially relevant documents, Feb. 11, 2016, Fuchs et al.
U.S. Appl. No. 15/068,323 including its ongoing prosecution history, including without limitation Office Actions, Amendments, Remarks, and any other potentially relevant documents, Mar. 11, 2016, Razzaque et al.
U.S. Appl. No. 15/182,346 including its ongoing prosecution history, including without limitation Office Actions, Amendments, Remarks, and any other potentially relevant documents, Jun. 14, 2016, Razzaque et al.
U.S. Appl. No. 15/199,630 including its ongoing prosecution history, including without limitation Office Actions, Amendments, Remarks, and any other potentially relevant documents, Jun. 30, 2016, Razzaque et al.
"3D Laparoscope Technology," http://www.inneroptic.com/tech_3DL.htm, copyright 2007 InnerOptic Technology, Inc. printed Sep. 19, 2007, 2 pages.
"Cancer Facts & Figures 2004," www.cancer.org/downloads/STT/CAFF_finalPWSecured.pdf, copyright 2004 American Cancer Society, Inc., printed Sep. 19, 2007, 60 pages.
Cancer Prevention & Early Detection Facts & Figures 2004; National Center for Tobacco-Free Kids; 2004; American Cancer Society; USA.
"David Laserscanner <-Latest News <- Institute for Robotics and Process Control <- Te . . . ," http://www/rob.cs.tu-bs.de/en/news/david, printed Sep. 19, 2007, 1 page.
"Laser scanned 3d model Final" video, still image of video attached, http://www.youtube.com/watch?v+DaLglgmoUf8, copyright 2007 YouTube, LLC, printed Sep. 19, 2007, 2 pages.
"Olympus Endoscopic Ultrasound System," www.olympusamerica.com/msg_section/download_brochures/135_b_gfum130.pdf, printed Sep. 20, 2007, 20 pages.
"Point Grey Research Inc.—Imaging Products—Triclops SDK Samples," http://www.ptgrey.com/products/triclopsSDK/samples.asp, copyright 2007 Point Grey Research Inc., printed Sep. 19, 2007, 1 page.
"Robbins, Mike—Computer Vision Research—Stereo Depth Perception," http://www.compumike.com/vision/stereodepth.php, copyright 2007 Michael F. Robbins, printed Sep. 19, 2007, 3 pages.
"RUE, Registered Ultrasound-Endoscope," copyright 2007 InnerOptic Technology, Inc., 2 pages.
Advertisement, "Inspeck 3DC 3D Capturor," Inspeck 3DC 3D Capturor (www.inspeck.com), 1998.
Advertisement, "Virtual 3D High Speed Non-Contact Surface Perception," Virtual 3-D Technologies Corporation (www.virtual3dtech.com)., Dec. 21, 1998.
Advertisements, "Virtuoso," Visual Interface, Inc. (www.visint.com), Dec. 21, 1998.
Akka, "Automatic Software Control of Display Parameters for Stereoscopic Graphics Images," SPIE Volume 1669: Stereoscopic Displays and Applications III, pp. 31-38 (1992).
Ali et al., "Near Infrared Spectroscopy and Imaging to Probe Differences in Water Content in Normal and Cancer Human Prostate Tissues," Technology in Cancer Research & Treatment; Oct. 2004; 3(5):491-497; Adenine Press.

Aylward et al., Analysis of the Parameter Space of a Metric for Registering 3D Vascular Images, in W. Niessen and M. Viergever (Eds.): MICCAI 2001, LNCS 2208, pp. 932-939, 2001.
Aylward et al., Registration and Analysis of Vascular Images, International Journal of Computer Vision 55(2/3), 123-138, 2003.
Aylward, et al., Intra-Operative 3D Ultrasound Augmentation, Proceedings of the IEEE International Symposium on Biomedical Imaging, Washington, Jul. 2002.
Azuma et al., "Improving Static and Dynamic Registration in an Optical See-Through HMD," Paper Presented at SIGGRAPH '94 Annual Conference in Orlando, FL, 17 pages (1994).
Azuma, "A Survey of Augmented Reality," Presence: Teleoperators and Virtual Environments 6, 4:1-48 (Aug. 1997).
Badler et al., "Simulating Humans: Computer Graphics, Animation, and Control," Oxford University Press (1993).
Bajura, Michael et al., "Merging Virtual Objects with the Real World: Seeing Ultrasound Imagery within the Patient," Computer Graphics, Proceedings of SIGGRAPH 1992, vol. 26(2), pp. 203-210, available from www.cs.unc.edu/~fuchs/publications/MergVirtObjs92.pdf, printed Sep. 20, 2007, 8 pages.
Benavides et al., "Multispectral digital colposcopy for in vivo detection of cervical cancer," Optics Express; May 19, 2003; 11(10) Optical Society of America; USA.
Beraldin, J.A. et al., "Optimized Position Sensors for Flying-Spot Active Triangulation Systems," Proceedings of the Fourth International Conference on a 3-D Digital Imaging and Modeling (3DIM), Banff, Alberta, Canada, Oct. 6-10, 2003, pp. 334-341, NRC 47083, copyright 2003 National Research Council of Canada, http://iit-iti.nrc-cnrc.gc.ca/iit-publications-iti/docs/NRC-47083.pdf, printed Sep. 19, 2007, 9 pages.
Billinghurst, M. et al., Research Directions in Handheld AR; Int. J. of Virtual Reality 5(2),51-58 (2006).
Blais, F., "Review of 20 Years of Range Sensor Development," Journal of Electronic Imaging, 13(1): 231-240, Jan. 2004, NRC 46531, copyright 2004 National Research Council of Canada, http://iit-iti.nrc-cnrc.gc.ca/iit-publications-iti/docs/NRC-46531.pdf, printed Sep. 19, 2007, 14 pages.
Bouguet, Jean-Yves, "Camera Calibration Toolbox for Matlab," www.vision.caltech.edu/bouguetj/calib_doc, printed Sep. 20, 2007, 5 pages.
Buxton et al.; "Colposcopically directed punch biopsy: a potentially misleading investigation," British Journal of Obstetrics and Gynecology; Dec. 1991; 98:1273-1276.
Caines, Judy S. et al. Stereotaxic Needle Core Biopsy of Breast Lesions Using a Regular Mammographic Table with an Adaptable Stereotaxic Device, American Journal of Roentgenology, vol. 163, No. 2, Aug. 1994, pp. 317-321. Downloaded from www.ajrorline.org on Jul. 10, 2013.
Cantor et al., "Cost-Effectiveness Analysis of Diagnosis and Management of Cervical Squamous Intraepithelial Lesions," Diagnostic Strategies for SILs; Feb. 1998; 91(2):270-277.
Catalano et al. "Multiphase helical CT findings after percutaneous ablation procedures for hepatocellular carcinoma." Abdom. Imaging, 25(6),2000, pp. 607-614.
Chiriboga et al., "Infrared Spectroscopy of Human Tissue. IV. Detection of Dysplastic and Neoplastic Changes of Human Cervical Tissue Via Infrared Microscopy," Cellular and Molecular Biology; 1998; 44(1): 219-229.
Crawford, David E. et al., "Computer Modeling of Prostate Biopsy: Tumor Size and Location—Not Clinical Significance—Determine Cancer Detection," Journal of Urology, Apr. 1998, vol. 159(4), pp. 1260-1264, 5 pages.
Deering, Michael "High Resolution Virtual Reality." Proceedings of SIGGRAPH '92, Computer Graphics, 26(2), 1992, pp. 195-202.
Depiero et al., "3-D Computer Vision Using Structured Light: Design, Calibration and Implementation Issues," The University of Tennessee, pp. 1-46, (1996).
Dodd, G.D. et al. "Minimally invasive treatment of malignant hepatic tumors: at the threshold of a major breakthrough." Radiographies 20(1),2000, pp. 9-27.
Drascic et al., "Perceptual Issues in Augmented Reality," SPIE vol. 2653: Stereoscopic Displays and Virtual Reality Systems III, pp. 123-134 (Feb. 1996).

(56) References Cited

OTHER PUBLICATIONS

Dumoulin, C.L. et al, Real-Time Position Monitoring of Invasive Devices Using Magnetic Resonance, Magnetic Resonance in Medicine, vol. 29, Issue 3, Mar. 1993, pp. 411-415.
Fahey et al., "Meta-analysis of Pap Test Accuracy; American Journal of Epidemiology," 1995 141(7):680-689; The John Hopkins University School of Hygiene and Public Health; USA.
Foxlin et al., "An Inertial Head-Orientation Tracker with Automatic Drift Compensation for Use with HMD's," Proceedings of the 1994 Virtual Reality Software and Technology Conference, Aug. 23-26, 1994, Singapore, pp. 159-173 (1994).
Fronheiser et al., Real-Time 3D Color Doppler for Guidance of Vibrating Interventional Devices, IEEE Ultrasonics Symposium, pp. 149-152 (2004).
Fuchs, Henry et al. "Augmented Reality Visualization for Laparoscopic Surgery," Proceedings of Medical Image Computing and Computer-Assisted Intervention (MICCAI) 1998, pp. 934-943, available from www.cs.unc.edu/~fuchs/publications/AugRealVis_LaparoSurg98.pdf, printed Sep. 20, 2007, 10 pages.
Fuchs, et al.: "Optimizing a Head-Tracked Stereo Display System to Guide Hepatic Tumor Ablation," Departments of Computer Sciences and Radiology, and School of Medicine, University of North Carolina at Chapel Hill; InnerOptic Technology, Inc. 2008.
Fuchs, et al.: "Virtual Environments Technology to Aid Needle Biopsies of the Breast," Health Care in the Information Age, Ch. 6, pp. 60-61, Presented in San Diego, Jan. 17-20, 1996, published by IOS Press and Ohmsha Feb. 1996.
Fuhrmann A. et al., Comprehensive calibration and registration procedures for augmented reality; Proc. Eurographics Workshop on Virtual Environments 2001,219-228 (2001).
Garrett, William F. et al., "Real-Time Incremental Visualization of Dynamic Ultrasound Volumes Using Parallel BSP Trees, "Proceedings of IEEE Visualization 1996, pp. 235-240, available from www.cs.unc.edu/~andrei/pubs/1996_VIS_dualBSP_Mac.pdf, printed Sep. 20, 2007, 7 pages.
Georgakoudi et al., "Trimodal spectroscopy for the detection and characterization of cervical precancers in vivo," American Journal of Obstetrics and Gynecology; Mar. 2002; 186(3):374-382; USA.
StereoMirror Technology Webpage, http://www.planar.com/products/flatpanel_monitors/stereoscopic/ (Printed Dec. 29, 2011).
Herline et al., Surface Registration for Use in Interactive, Image-Guided Liver Surgery, Computer Aided Surgery 5:11-17 (2000).
Holloway, R.; Registration Error Analysis for Augmented Reality; Presence: Teleoperators and Virtual Environments 6(4), 413-432 (1997).
Hornung et al., "Quantitative near-infrared spectroscopy of cervical dysplasia in vivo," Human Reproduction; 1999; 14(11):2908-2916; European Society of Human Reproduction and Embryology.
Howard, M.D., et al.: "An Electronic Device for Needle Placement during Sonographically Guided Percutaneous Intervention", Radiology 2001; 218:905-911.
InnerAim Brochure; 3D Visualization Software for Simpler, Safer, more Precise Aiming, Published no earlier than Apr. 1, 2010.
InVision System Brochure; A "GPS" for Real-Time 3D Needle Visualization & Guidance, Published no earlier than Mar. 1, 2008.
InVision User Manual; Professional Instructions for Use, Published no earlier than Dec. 1, 2008.
Jacobs, Marco C. et al., "Managing Latency in Complex Augmented Reality Systems," ACM SIGGRAPH Proceedings of the Symposium of Interactive 3D Graphics 1997, pp. 49-54, available from www.cs.unc.edu/~us/Latency//ManagingRelativeLatency.html, printed Sep. 20, 2007, 12 pages.
Jolesz, Ferenc A, M.D., et al. MRI-Guided Laser-Induced Interstitial Thermotherapy: Basic Principles, SPIE Institute on Laser-Induced Interstitial Thermotherapy (L1TT), Jun. 22-23, 1995, Berlin, Germany.
Kadi, A Majeed, et al., Design and Simulation of an Articulated Surgical Arm for Guiding Sterotactic Neurosurgery, SPIE vol. 1708 Applications of Artificial Intelligence X: Machine Vision and Robotics (1992). Downloaded from: http://proceedings.spiedigitallibrary.org/ on Jul. 11, 2013.
Kanbara et al., "A Stereoscopic Video See-through Augmented Reality System Based on Real-time Vision-Based Registration," Nara Institute of Science and Technology, pp. 1-8 (2000).
Kato, Amami, et al., A frameless, armless navigational system for computer-assisted neurosurgery, Journal of Neurosurgery, vol. 74, No. 5, May 1991, pp. 845-849.
Keller et al., "What is it in Head Mounted Displays (MDs) that really make them all so terrible?," pp. 1-8 (1998).
Lass, Amir, "Assessment of Ovarian Reserve," Human Reproduction, 2004, vol. 19(3), pp. 467-469, available from http://humrep.oxfordjournals.orgcgi/reprint/19/3/467, printed Sep. 20, 2007, 3 pages.
Lee, et al., "Modeling Real Objects Using Video See-Through Augmented Reality," Proceedings of the Second International Symposium on Mixed Reality, ISMR 2001, pp. 19-26 (Mar. 14-15, 2001).
Lee et al., "Modeling Real Objects Using Video See-Through Augmented Reality," Presence, 11(2):144-157 (Apr. 2002).
Leven et al., DaVinci Canvas: A Telerobotic Surgical System with Integrated, Robot-Assisted, Laparoscopic Ultrasound Capability, in J. Duncan and G. Gerig (Eds.): MICCAI 2005, LNCS 3749, pp. 811-818, 2005.
Levy, et al., An Internet-Connected, Patient Specific, Deformable Brain Atlas Integrated into a Surgical Navigation System, Journal of Digital Imaging, vol. 10, No. 3. Suppl. 1 Aug. 1997: pp. 231-237.
Livingston, Mark A. et al., "Magnetic Tracker Calibration for Improved Augmented Reality Registration," Presence: Teleoperators and Virtual Environments, 1997, vol. 6(5), pp. 532-546, available from www.cs.unc.edu/~andrei/pubs/1997_Presence_calibr.pdf, printed Sep. 20, 2007, 14 pages.
Matsunaga et al., "The Effect of the Ratio Difference of Overlapped Areas of Stereoscopic Images on each Eye in a Teleoperalion," Stereoscopic Displays and Virtual Reality Systems VII, Proceedings of SPIE, 3957:236-243 (2000).
Meehan, Michael et al., "Effect of Latency on Presence in Stressful Virtual Environment," Proceedings of IEEE Virtual Reality 2003, pp. 141-148, available from http://www.cs.unc.edu/~eve/pubs.html, printed Sep. 20, 2007, 8 pages.
Milgram et al., "Adaptation Effects in Stereo due to Online Changes in Camera Configuration," SPIE vol. 1669-13, Stereoscopic Displays and Applications III, 17 pages (1992).
Mitchell et al., "Colposcopy for the Diagnosis of Squamous Intraepithelial lesions: A metaanalysis," Obstetrics and Gynecology; Apr. 1998; 91(4):626-631.
Nakamoto et al., 3D Ultrasound System Using a Magneto-optic Hybrid Tracker for Augmented Reality Visualization in Laparoscopic Liver Surgery, in T. Dohi and R. Kikinis (Eds.): MICCAI 2002, LNCS 2489, pp. 148-155, 2002.
Nordstrom et al., "Identification of Cervical Intraepithelial Neoplasia (CIN) Using UV-Excited Fluorescence and Diffuse-Reflectance Tissue Spectroscopy," Lasers in Surgery and Medicine; 2001; 29; pp. 118-127; Wiley-Liss, Inc.
Ohbuchi et al. "An Incremental Volume Rendering Algorithm for Interactive 3D Ultrasound Imaging", UNC-CH Computer Science Technical Report TR91-003, (1991).
Ohbuchi et al., "Incremental Volume Reconstruction and Rendering for 3D Ultrasound Imaging," Visualization in Biomedical Computing, SPIE Proceedings, pp. 312-323, (Oct. 13, 1992).
Ohbuchi, "Incremental Acquisition and Visualization of 3D Ultrasound Images," Ph.D. Dissertation, UNC-CH Computer Science Technical Report TR95--023, (1993).
Pogue, Brian W. et al., "Analysis of acetic acid-induced whitening of high-grade squamous intraepitheliallesions," Journal of Biomedical Optics; Oct. 2001; 6(4):397-403.
Raij, A.B., et al., Comparing Interpersonal Interactions with a Virtual Human to Those with a Real Human; IEEE Transactions on Visualization and Computer Graphics 13(3), 443-457 (2007).
Raz et al, Real-Time Magnetic Resonance Imaging-Guided Focal Laser Therapy in Patients with Low-Risk Prostate Cancer, European Urology 58, pp. 173-177. Mar. 12, 2010.

(56) References Cited

OTHER PUBLICATIONS

Robinett et al., "A Computational Model for the Stereoscopic Optics of a Head-Mounted Display," SPIE vol. 1457, Stereoscopic Displays and Applications II, pp. 140-160 (1991).
Rolland et al., Towards Quantifying Depth and Size Perception in Virtual Environments, Presence: Teleoperators and Virtual Environments, Winter 1995, vol. 4, Issue 1, pp. 1-21 and 24-49.
Rosenthal, Michael et al., "Augmented Reality Guidance for Needle Biopsies: An Initial Randomized, Controlled Trial in Phantoms," Proceedings of Medical Image Analysis, Sep. 2002, vol. 6(3), pp. 313-320, available from www.cs.unc.edu/~fuchs/publications/AugRealGuida_NeedleBiop02.pdf, printed Sep. 20, 2007, 8 pages.
Rosenthal, Michael et al., "Augmented Reality Guidance for Needle Biopsies: A Randomized, Controlled Trial in Phantoms," Proceedings of MICCAI 2001, eds. W. Niessen and M. Viergever, Lecture Notes in Computer Science, 2001, vol. 2208, pp. 240-248, available from www.cs.unc.edu/~us/AugmentedRealityAssistance.pdf, printed Sep. 20, 2007, 9 pages.
Screenshots from video produced by the University of North Carolina, produced circa 1992.
"Sony Introduces Head-Mounted Display for Endoscopic Surgery" (Jul. 23, 2013), retrieved Sep. 27, 2016, 5 pages, available at http://www.medgaget.com/2013/07/sony-introduces-head-mounted-display-for-endoscopic-surgery.html.
"Sony Introduces 'head-mount image processing unit' for endoscopic image display" (Jul. 23, 2013), retrieved Sep. 27, 2016, 8 pages, available at http://www.sony.net/SonyInfo/News/Press/201307/13-085E/index.html.
State et al., "Case Study: Observing a Volume Rendered Fetus within a Pregnant Patient," Proceedings of IEEE Visualization 1994, pp. 364-368, available from www.cs.unc.edu/~fuchs/publications/cs-ObservVolRendFetus94.pdf, printed Sep. 20, 2007, 5 pages.
State et al., "Interactive Volume Visualization on a Heterogeneous Message-Passing Multicomputer," Proceedings of 1995 Symposium on Interactive 3D Graphics, 1995, pp. 69-74, 208, available from www.cs.unc.edu/~andrei/pubs/1995_I3D_vol2_Mac.pdf, printed Sep. 20, 2007.
State et al., "Simulation-Based Design and Rapid Prototyping of a Parallax-Free, Orthoscopic Video See-Through Head-Mounted Display," Proceedings of International Symposium on Mixed and Augmented Reality (ISMAR) 2005, available from www.cs.unc.edu/~andrei/pubs/2005_ISMAR_VSTHMD_design.pdf, printed Sep. 20, 2007, 4 pages.
State et al., "Stereo Imagery from the UNC Augmented Reality System for Breast Biopsy Guidance" Proc. Medicine Meets Virtual Reality (MMVR) 2003 (Newport Beach, CA, Jan. 22-25, 2003).
State et al., "Superior Augmented Reality Registration by Integrating Landmark Tracking and Magnetic Tracking," ACM SIGGRAPH Computer Graphics, Proceedings of SIGGRAPH 1996, pp. 429-438, available from www.cs.princeton.edu/courses/archive/fall01/cs597d/papers/state96.pdf, printed Sep. 20, 2007, 10 pages.
State et al., "Technologies for Augmented Reality Systems: Realizing Ultrasound-Guided Needle Biopsies," Proc. SIGGRAPH 96 (New Orleans, LA, Aug. 4-9,1996). In Computer Graphics Proceedings, Annual Conference Series, 1996, ACM SIGGRAPH, pp. 439-446.
State, Andrei "Exact Eye Contact with Virtual Humans." Proc. IEEE International Workshop on Human Computer Interaction 2007 (Rio de Janeiro, Brazil, Oct. 20, 2007), pp. 138-145.
State, et al.: Contextually Enhanced 3D Visualization for Multi-Born Tumor Ablation Guidance, Departments of Computer Science and Radiology, and School of Medicine, University of North Carolina at Chapel Hill; InnerOptic Technology, Inc. 2008, Chapel Hill, NC, pp. 70-77.
Symons et al., "What are You Looking at? Acuity for Triadic Eye Gaze," J. Gen. Psychology 131(4), pp. 451-469 (2004).
Takacs et al., "The Virtual Human Interface: A Photorealistic Digital Human," IEEE Computer Graphics and Applications 23(5), pp. 38-45 (2003).
Takagi et al., "Development of a Stereo Video See-through HMD for AR Systems," IEEE, pp. 68-77 (2000).
Takayama et al., "Virtual Human with Regard to Physical Contact and Eye Contact," Entertaining Computing 2005, LNCS, vol. 3711, pp. 268-278 (2005).
Ultraguide 1000 System, Ultraguide, www.ultraguideinc.com, 1998.
Van Staveren et al., "Light Scattering in Intralipid-10% in the wavelength range of 400-1100 nm," Applied Optics; Nov. 1991; 30(31):4507-4514.
Viola et al., "Alignment by Maximization of Mutual Information," International Journal of Computer Vision, vol. 24, No. 2, pp. 137-154 (1997).
Viola, Paul A., Alignment by Maximization of Mutual Information, Ph.D. Dissertation, MIT-Artificial Intelligence Laboratory Technical Report No. 1548 (Jun. 1995), 156 pages.
Ware et al., "Dynamic Adjustment of Stereo Display Parameters," IEEE Transactions on Systems, Many and Cybernetics, 28(1):1-19 (1998).
Watson et al., "Using Texture Maps to Correct for Optical Distortion in Head-Mounted Displays," Proceedings of the Virtual Reality Annual Symposium '95, IEEE, pp. 1-7 (1995).
Welch, Hybrid Self-Tracker: An Inertial/Optical Hybrid Three-Dimensional Tracking System, University of North Carolina Chapel Hill Department of Computer Science, TR 95-048 (1995).
Yinghui et al., Real-Time Deformation Using Modal Analysis on Graphics Hardware, Graphite 2006, Kuala Lumpur, Malaysia, Nov. 29-Dec. 2, 2006.
Zitnick et al., "Multi-Base Stereo Using Surface Extraction," Visual Interface Inc., (Nov. 24, 1996).

\* cited by examiner

MEDICAL DEVICE APPROACHES

CROSS-REFERENCE TO RELATED APPLICATION

This application claims the benefit of U.S. Provisional Application No. 62/195,676, filed Jul. 22, 2015, which is incorporated by reference herein in its entirety for all purposes. Any and all applications for which a foreign or domestic priority claim is identified in the Application Data Sheet as filed with the present application are incorporated by reference under 37 CFR 1.57 and made a part of this specification.

BACKGROUND

Image-guided surgery makes use of imaging to aid the surgeon to perform more effective or more accurate surgery.

DETAILED DESCRIPTION

Implementations disclosed herein provide systems, methods, and apparatus for guidance tasks related to pose and/or emplacement of medical devices. Certain embodiments pertain to systems for facilitating visualization of medical imaging device scanning approaches and/or needle approaches for surgical applications. Visualization of medical device poses and/or emplacements can allow a user to select a desirable needle insertion point to minimize insertion or repositioning attempts.

Systems and methods described herein can be used to determine one or more poses and/or emplacements of various medical devices. The term "emplacement" and the term "pose" as used herein are broad terms encompassing their plain and ordinary meanings and can refer to, without limitation, position, orientation, the combination of position and orientation, or any other appropriate location information.

Figure 3:
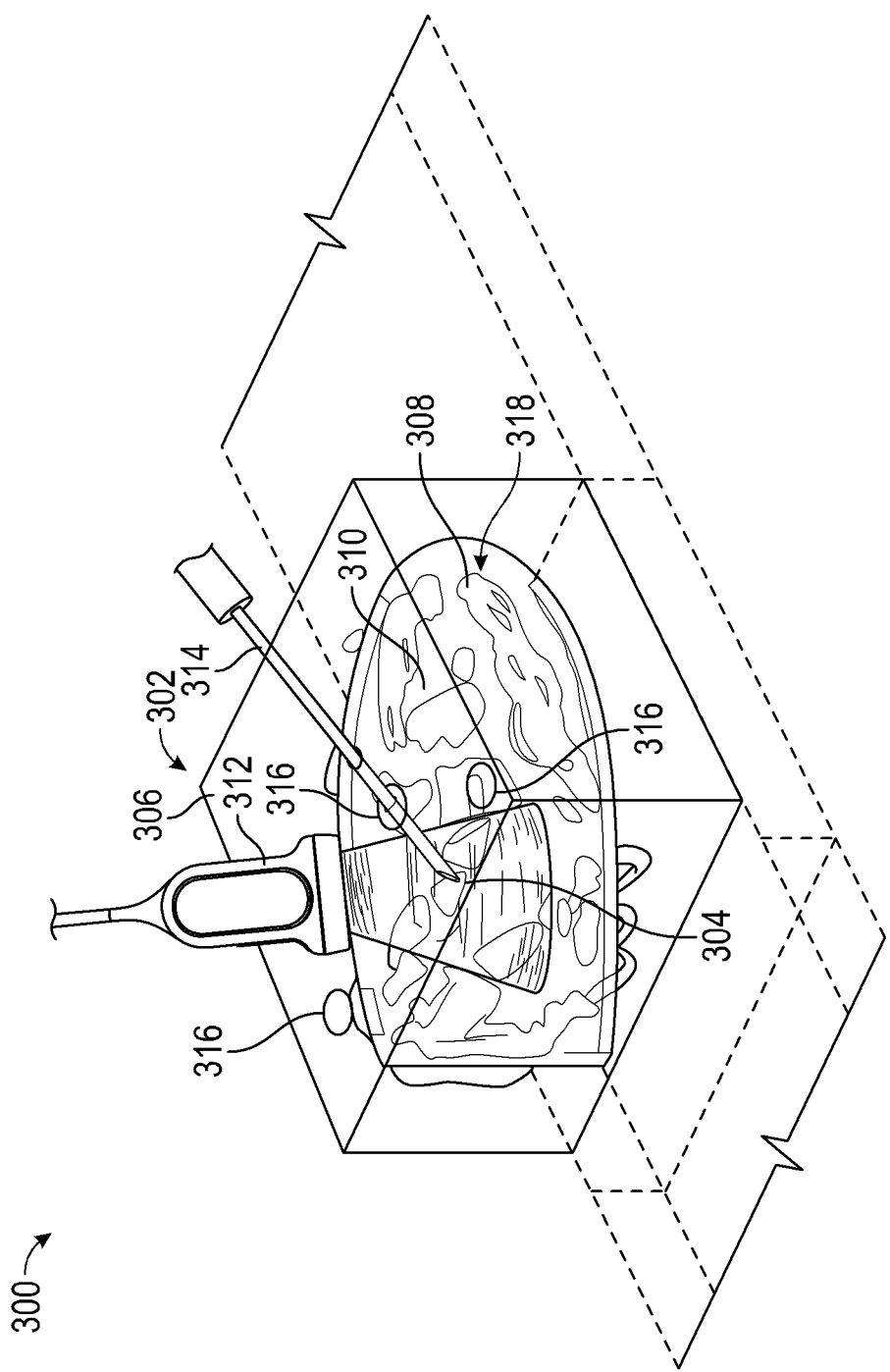
FIG. 3 illustrates a three-dimensional volumetric medical image with exemplary image scanning and needle approach paths.

As discussed elsewhere herein, there are numerous types of volumetric or 3D data that various embodiments of the guidance system herein can display. The term "volumetric medical image" is a broad term that encompasses its ordinary and customary meaning, and includes, without limitation any data in a volume or 3D space that can be displayed. The volumetric medical image can include, without limitation, one or more of a CT scan, an MRI, other 3D intraoperative or preoperative imaging data, other volume data, segmented internal organs, segmented blood vessels, annotations, tumors, etc. Such data can include CT scans, MRI, PET, 3D ultrasound, and any of numerous other types of 3D data. In some embodiments, in order to display 3D data on a 2D interface, such as a computer screen, or even a 3D interface, such as a head-mounted display or other 3D display, a subset of the data is chosen to display. This subset of data can include axis-aligned slices, the entire volume, or a sub-volume of the data. An inherent difficulty with image guidance is the display of three dimensions of data on a two-dimensional screen or "dual eye" three-dimensional display. When displaying 3D data, such as CT scans, a system might only display a single plane, or show three orthogonal planes separately on the screen. The data can also be shown as a volumetric 'block' of data, as shown in FIG. 3.

Figure 1A:
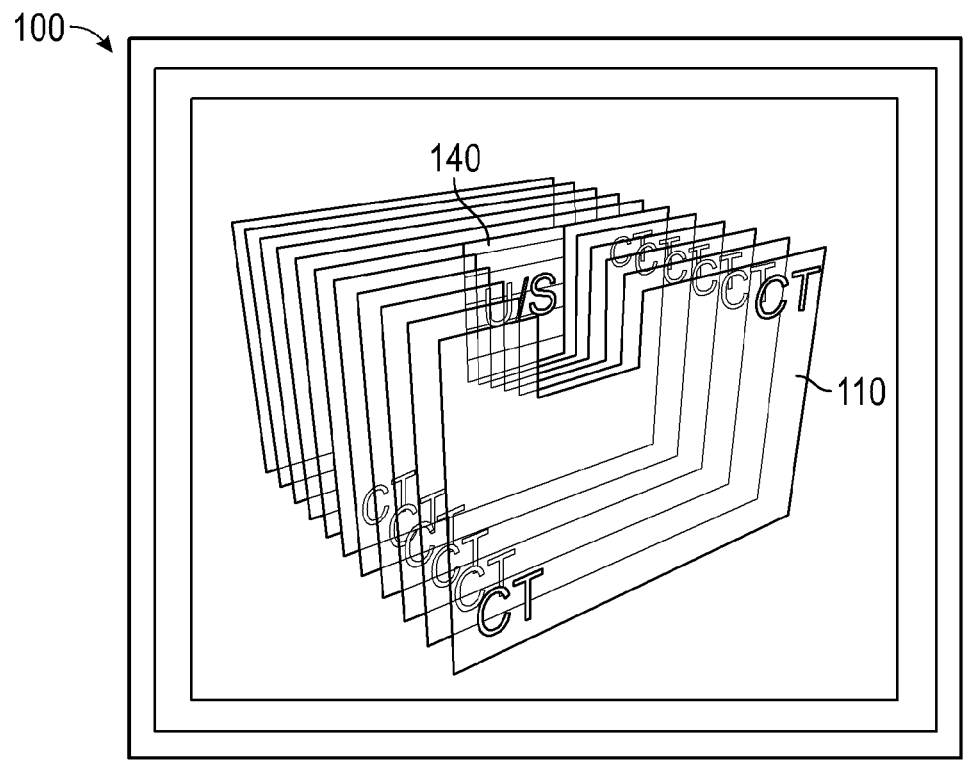
FIGS. 1A and 1B illustrate exemplary volumetric medical images for image-guided medical procedures.
Figure 1B:
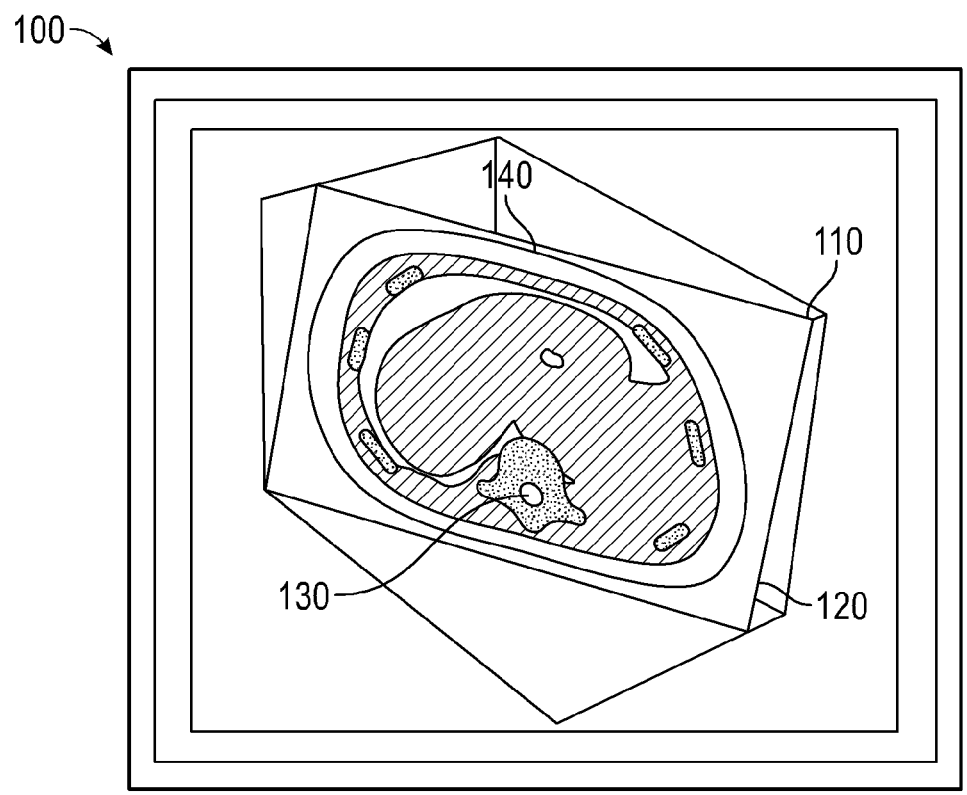

FIGS. 1A and 1B illustrate exemplary volumetric medical images 100 for image-guided medical procedures. The image 100 can be obtained based on any medical imaging technology as described herein, such as ultrasound, CT scan, MRI, open-magnet MRI, optical coherence tomography, positron emission tomography ("PET") scans, fluoroscopy, ultrasound, or other preoperative, or intraoperative 2D or 3D anatomical imaging data. The image 100 can include multiple planes or slices 110 of image data. In some aspects, the volumetric medical image 100 can be obtained as a plurality of slices 110 from an imaging device configured to perform multiple 2D scans, or can be obtained as 3D volume data from an imaging device configured to generate 3D data. Where volumetric imagery is obtained from 2D scans, the planes or slices 110 can be the slices as obtained from the 2D scans, or they can be modified and/or generated to be, for example, parallel to the plane of a region of interest.

As depicted in FIG. 1B, a plane or slice 110 of the volumetric medical image 100 can include a cross-sectional view of a portion of a subject 120. In various embodiments, the location and orientation of the plane or slice 110 can be selected automatically based on detected structures within the volumetric medical image 100, or can be selected manually by a user. For example, the location and orientation can be selected so as to provide a cross-sectional view of a target structure 130, such as a lesion, tumor, or other structure.

In some embodiments, a region of interest 140 can be selected within a plane or slice 110. The region of interest 140 can be selected automatically or by a user, for example, based on a location of an emplacement sensor associated with a medical device (e.g., an ultrasound probe) manipulated by the user. In some implementations, the system can utilize and/or display imagery associated with the medical device (e.g., ultrasound image data obtained from an ultrasound probe) in addition to (e.g., superimposed upon) the volumetric image data. The data shown in the region of interest can be any appropriate visualizable medical data, not limited to ultrasound or CT data. Further, the data displayed outside of the region of interest can be any visualizable medical data, and can even be from the same data set as the data shown in the region of interest. For example, MRI data can be shown in fading planes outside of the region of interest and in focus (and visualizable through a tunnel) inside the region of interest. Further, annotation can be displayed along with the rendering of the visualizable medical data inside and/or outside of the region of interest. In this manner, a user can see the annotations in the context of the visualizable medical data.

In various embodiments, more than one set of visualizable medical data can be rendered. Each one can be rendered in a different manner. For example, they can be rendered with different transparencies, brightnesses, contrast, colors, etc. Further, one or more can be rendered with a different transparency, brightness, contrast or color as distance from the region of interest increases. For example, brightness can decrease and/or transparency can increase further from the region of interest 140.

Figure 2:
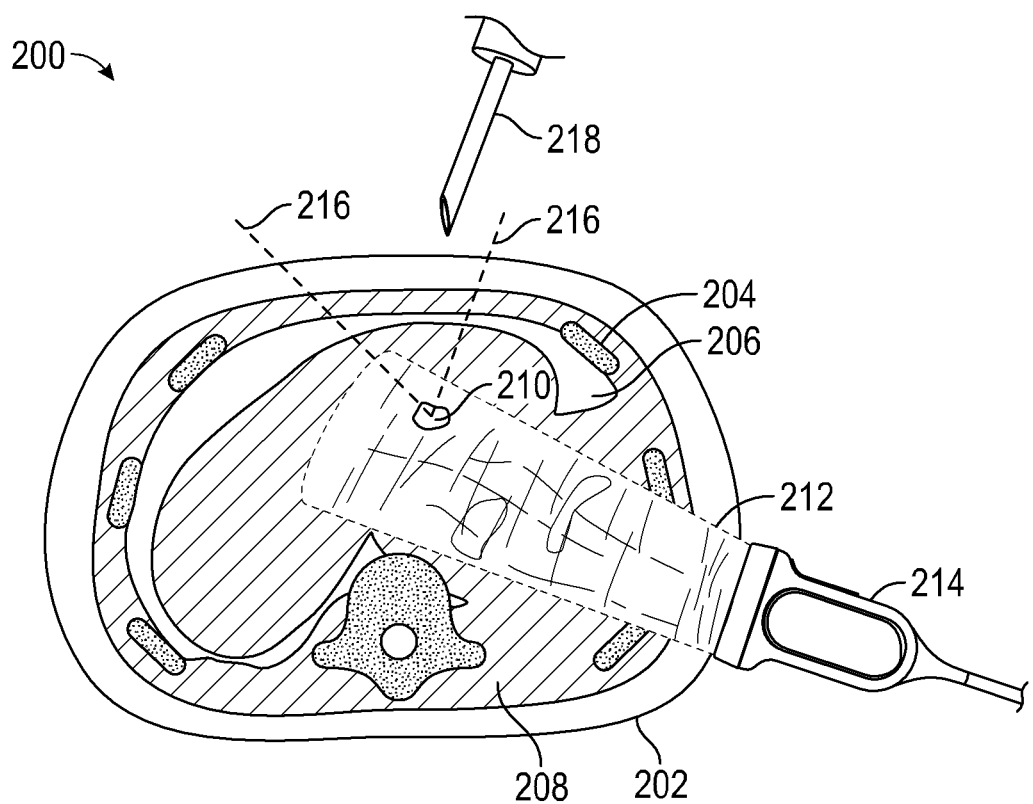
FIG. 2 illustrates a two-dimensional slice of a volumetric medical image with exemplary image scanning and needle approach paths.

FIG. 2 illustrates a 2D slice 200 of a volumetric medical image with exemplary image scanning and needle approach paths as determined by a guidance system. The exemplary slice 200 depicted in FIG. 2 includes a cross-sectional image of a torso of a patient, including sections of skin 202, bone 204, gas 206, and other internal tissues 208, as well as a target structure 210 (non-limiting examples: a lesion, tumor, or other target). Also depicted are a suggested scanning path 212 for an ultrasound probe and suggested approach paths 216 for a needle 218 or other invasive medical device.

The target structures 210 can be identified in a variety of ways. In some embodiments, the guidance system can allow a user to mark a target by interacting with the display of the volumetric medical image. For example, consider a procedure where the doctor is using the guidance system with an ablation needle 218 and an ultrasound probe 214. The doctor can mark the target structure 210 by pressing a button on a keyboard or mouse, touching a screen, pointing with a medical device, gesturing or issuing a verbal command, or with any other appropriate method, as described in greater detail in U.S. application Ser. No. 14/166,179, entitled, SYSTEMS, METHODS, APPARATUSES, AND COMPUTER-READABLE MEDIA FOR IMAGE MANAGEMENT IN IMAGE-GUIDED MEDICAL PROCEDURES, and Ser. No. 13/014,596, entitled, IMAGE ANNOTATION IN IMAGE-GUIDED MEDICAL PROCEDURES, each of which is incorporated herein by reference in its entirety.

In some embodiments, the system can detect the target structure 210 within an image stream obtained from an imaging device manipulated by the user (e.g., an ultrasound probe 214). In certain embodiments, the location of the target structure 210 can be marked at the point where a needle 218 intersects with the ultrasound image plane, where the needle's projection intersects with the ultrasound image plane, or any other appropriate relationship (such as at the location of the tip of the needle). For example, when a physician identifies a target structure 210 within the ultrasound image, she can point to it using the needle 218 even if the needle 218 is outside the body of the patient. The physician (or assistant) can press, for example, a button or foot pedal, which informs the image guidance system to store the 3D position of this target structure 210. In some embodiments, the target structure 210 can be identified based at least in part on the amount of time the physician spends observing an object or the amount of time that a medical device, or corresponding emplacement sensor, is located at a particular emplacement. For example, if a lesion or other abnormal structure is detected within the ultrasound image, and the physician keeps the probe 214 in the same location for a threshold time period (e.g., 3 seconds, 5 seconds, 10 seconds, 15 seconds, or longer), the guidance system can determine that the object is a target structure 210 and store its location.

In certain embodiments, the system can identify multiple target structures 210. For example, physicians, during some liver ablation procedures or other procedures, can manage fifteen target structures 210, or even more. The guidance system can store and display any number of target structures 210 concurrently. If there is more than one target structure 210 in view, the image guidance system can display a number or other indicator next to each one (not pictured). In some embodiments, in order to reduce visual clutter if there are many target structures 210, those target structures 210 which are closer to the ultrasound image plane can be drawn more saliently or vividly (with more bold color and thicker lines) while the points that are far away are drawn less saliently (more transparent, blurred, muted colors, etc.).

In addition, to identifying a target structure, the system can analyze the various types of tissue within the medical image to determine an approach path for the medical device. For example, ultrasound waves emitted by an ultrasound probe 214 may be able to travel through soft tissues 208 of a patient, but can be blocked or scattered by denser tissues such as bone 204, or by regions of lower density, such as gas 208. An ablation needle 218 may be able to travel through soft tissues 208 and/or regions of gas 208, but may be unable to travel through bone 204. In addition, needle approach paths can be chosen so as to avoid critical or delicate regions such as blood vessels or vital organs (not shown), even though such regions do not present an obstacle to ultrasound scanning.

Thus, when a 2D slice 200 is obtained, the guidance system can analyze the image to determine the tissue type or density of various regions of the image. In some embodiments, the guidance system can analyze the slice 200 based on an intensity of some or all pixels or voxels within the slice 200. The system can determine a radiodensity or intensity of voxels based on the Hounsfield unit (HU) scale or other suitable scale. For example, an intensity of greater than 700 HU can indicate bone, while an intensity of between −1000 HU and −350 HU can indicate intestinal gas. However, it will be understood that different imaging devices can output different HU for different types of tissue or can use different scales for intensity of voxels.

In some embodiments, the system can analyze the intensity level for each voxel of the medical image to determine the tissue type and/or object density. In certain embodiments, the system can use edge detection to identify objects, for example, to identify the location of skin 202 within the image slice 200. In some aspects, the system can use known HU values of critical or delicate regions (e.g., large blood vessels, heart, etc.) to identify the critical or delicate regions. Furthermore, in certain embodiments, such as with medical images involving the chest or abdomen of a patient, the system can analyze one or more image slices 200 taken at different parts of the breathing cycle. In this way, the system can determine the emplacement of the objects within the image slices at different parts of the breathing cycle and to identify deformations of the objects caused by breathing. It will be understood that the system can use other scales or measurements to identify the objects in the medical image, such as, but not limited to, manual or automatic segmentation, annotation, as described in greater detail in U.S. application Ser. No. 13/014,596, entitled, IMAGE ANNOTATION IN IMAGE-GUIDED MEDICAL PROCEDURES, previously incorporated herein by reference, etc.

In addition to analyzing the content of the medical image, the system can determine one or more medical device approach paths 216 to the target structure 210 from an approach region. The approach region can correspond to a surface or perimeter of the medical image and/or a desired start point, surface, or perimeter within the medical image. For example, the system can determine and display paths to the target structure from the surface of the medical image and/or from a particular structure within the medical image, such as the skin, an intestine, etc. In certain embodiments, to identify medical device approach paths 216 to the target structure 210, the system can analyze a plurality of paths between the target structure 210 and the approach region of the medical image.

In some cases, the system can use ray tracing or ray casting to identify paths to the target structure from the approach region of the image. For example, the system can analyze voxels along a particular path to identify paths between the target structure 210 and the approach region.

In some embodiments, the system can use one or more rendered images to identify paths to the target structure. For example, the system can render one more images from the perspective of the target to the approach region. In some embodiments, the system can treat the target as a point-of-view location and capture the voxels located between the target and the approach region, similar to a camera taking a picture. In certain embodiments, the volume of the captured voxels can generally correspond to a trapezoid, cone, frustum, or other shape.

In certain embodiments, the one or more images can be from different angles with respect to the target. As a non-limiting example, if the approach region is the surface of the 3D volume and the target is located within the 3D volume, the system can render six images (each one from the perspective of a different side of a cube corresponding to the target). It will be understood that fewer or more images can be rendered from different perspectives, as desired.

The system can render the captured images (or captured voxels). As part of the rendering process, the system can map the captured volume of voxels or imaged volume to an image area or region. In addition, the system can identify how to treat the different voxels during the rendering process. For example, the system can average the voxels that are to be located on a point of the image area, use the minimum or maximum voxel for the point of the image area, etc. In certain embodiments, the system can identify voxels that do not satisfy a density threshold (or otherwise not to be used for a medical device approach), as described in greater detail below, to be rendered differently than voxels that satisfy the density threshold. For example, if any one of the voxels that are to be mapped to a location in the image area do not satisfy the density threshold, the system can color code the location, such as by whiting or blacking it out, etc.

The one or more rendered images can be applied or mapped to the approach region of the 3D volume for viewing. With continued reference to the example, the system can map the one or more images to the surface of the 3D volume. Accordingly, a user can view the images on the approach region. In some embodiments, the system can also analyze the rendered images (non-limiting examples: using voxel intensities, edge detection, etc.) to identify locations in the rendered image in which the approach region is visible. The identification of the approach region within the image can indicate a direct path between the approach region and the target structure 210.

In certain embodiments, the system can analyze the image slice 200 along a series of circular paths of increasing or decreasing radius and centered on the target structure 210 (e.g., from the target structure 210 outward, or from the approach region). For example, the system can analyze the voxels within a sphere and then expand the sphere and analyze voxels within the expanded sphere. Analyzing a series of circular paths can be efficient, as angular segments of a circle that are deemed unacceptable for an approach path (e.g., due to the presence of bone) can be eliminated and the same angular regions can be omitted from the analysis of later circular paths, reducing processing time.

In analyzing the various paths between the target structure 210 to the approach region, the system can apply one or more criteria to identify one or more medical device approaches 216. For example, the system can use a density threshold, characteristics of a medical device, such as length, width, thickness, diameter, scan length, scan width, number transducer crystals, etc., to identify one or more medical device approaches.

In certain cases, the system can use characteristics of the medical device to determine the medical device approach. The medical device can be an invasive medical device, such as, but not limited to, biopsy needles, ablation needles, surgical needles, nerve-block needles, or other needles, electrocautery device, catheters, stents, laparoscopes or laparoscopic cameras, ultrasound transducers, or other instruments that enter a part of the body, or a non-invasive medical device that does not enter the body, such as, but not limited to, ultrasound transducers, probes, other external imaging devices, or other external devices, etc. The medical devices can also include medical imaging devices that provide or aid in the selection or generation of medical images for display. In some embodiments, the medical imaging device can be any device that is used to select a particular medical image for display or generate medical images. The medical imaging devices can include invasive medical devices, such as laparoscopic cameras or invasive ultrasound transducers, and non-invasive medical devices, such as external ultrasound transducers.

Depending on the medical device used, the medical device approach can be different. For example, each medical device can have unique dimensions, such as width, length, and/or thickness. Similarly, medical imaging devices can have different imaging depths, widths and/or thicknesses. In addition, medical imaging devices can use different scan frequencies, each of which can affect which tissue can be imaged. The system can use the various characteristics to determine the medical device approach.

In some embodiments, such as for invasive medical devices, the system can use the medical device's physical characteristics, such as its hardness or ability to pass through an object, deformability, curvature, length, width, thickness, and/or diameter to determine the medical device approach. Each invasive medical device can have its own physical characteristics that the system can use to determine the medical device approach. For example, the system can determine more medical device approaches for invasive medical devices that are longer, thinner, are more deformable, or have a smaller diameter. In some cases, the diameter, deformability, or thickness of the medical device can be different along its longitudinal axis. In such cases, the system can use the different thicknesses or deformability and location along the medical device axis to identify the medical device approaches.

With reference to FIG. 2, in some implementations, the system can eliminate paths 216 that pass through a region of bone 204, or other region through which the needle 218 is unable to pass. Similarly, the system can eliminate paths for the needle 218 that pass through a vital organ or a large blood vessel (not shown). In certain embodiments, the system can have information regarding the length of the needle 218, and can determine a maximum approach path length based at least in part on the length of the needle 218 and/or maximum reach of the needle 218. The system can exclude approach paths in which the distance from the approach region to the target structure 210 is longer than maximum approach length. In some embodiments, the system can include approach paths 216 that are wide and/or thick enough for the needle 218 to pass through, based on a known width and/or thickness of the needle 218.

In certain embodiments, such as for medical imaging devices, the system can use the imaging characteristics of the medical imaging device, such as, but not limited to, number of imaging sensors, number of transducer crystals, imaging frequency, imaging depth, resolution, fade, imaging width and/or imaging thickness to determine the medical device approach. In some cases, such as for invasive medical imaging devices, the system can also use the physical characteristics of the medical imaging device. In certain circumstances, the system can use the physical characteristics of a non-invasive medical imaging as well.

Similar to physical characteristics, each medical imaging device can have unique imaging characteristics that the system can use to determine the medical device approach. In certain embodiments, the system can determine more medical device approaches for medical imaging devices that have a larger imaging depth, larger imaging width, more imaging sensors, more transducer crystals, better resolution, less fade, or lower imaging frequency. For example, medical imaging devices with a larger imaging depth or width, more imaging sensors or more transducers can capture a larger image cross-section, which can enable the system to identify more potential paths. Similarly, the system can identify more medical device paths for medical imaging devices that have better resolution or fade less based on the distance from the imager, etc.

In addition, in some cases, imaging devices may unable to penetrate certain tissue depending on the frequency used. For example, many ultrasound transducers are unable to penetrate bone or gas and optical image sensors cannot penetrate tissue. Accordingly, the system can use the scan frequency or imaging type to identify medical device approaches. In addition, as described in greater detail above with reference to invasive medical devices, the physical characteristics of a medical imaging device can affect the number of medical device approaches identified by the system.

With continued reference to the embodiments illustrated in FIG. 2, the system can eliminate paths that pass through regions of gas 206 or bone 204 because the ultrasound probe 214 cannot penetrate the gas 206 or bone 204. The system 204 can use the imaging dimensions of the ultrasound probe to determine medical device paths 212 as well. For example, the ultrasound probe 214 can include a linear array of ultrasound crystals, each crystal configured for imaging along a path. The system can determine acceptable ultrasound scanning paths 212 where the unobstructed path has a 2D or 3D width of a threshold number of crystals.

In certain embodiments, the threshold number of crystals can be based on a number of crystals that have an unobstructed path to the target structure 210 and/or a number of crystals of the ultrasound probe 214. For example, the threshold number of crystals can be 25% or 50% of the total number of crystals of the ultrasound probe 214, and/or can be 1, 3, 5, 10, 15, or more crystals. In addition, the system can use the image depth of the ultrasound probe 214 determine the medical device approach paths 216. For example, the system can eliminate paths to the target structure 210 that are longer than the image depth of the ultrasound probe 210.

In some cases, the system can use a density threshold to identify the medical device approaches. As mentioned above, the density threshold can be based on the Hounsfield unit scale or similar scale, and can correspond to a minimum density, maximum density, or range of densities. In some embodiments, the system can identify objects and/or voxels that do not satisfy the density threshold (or are otherwise not to be used for a medical device approach) as obstructing objects. In certain embodiments, the system can exclude paths that intersect with obstructing objects. In addition, in some cases, the system can identify voxels or objects that have been annotated as not satisfying the density threshold or as obstructing objects.

In some embodiments, the density threshold can be static. For example, the system can identify objects having a density equal to or greater than bone as not satisfying the density threshold, irrespective of the medical device. In certain embodiments, such as when the density of critical tissue, such as heart tissue is known, the system can identify objects having the same density as the critical tissue as not satisfying the density threshold.

In certain embodiments, the density threshold can be based at least in part on a characteristic of the medical device. For example, gas within the image can satisfy the density threshold for a needle, but may not satisfy the threshold for an ultrasound device.

In some cases, the system can identify one or more semi-direct paths from the target structure 210 to the approach region. In certain embodiments, a semi-direct path may become available if a portion of the approach region or patient is deformed. For example, if a physician wants to access a portion of a patient under the rib cage, no direct path may be available. However, by compressing the abdomen or at a different time of the breathing cycling, a path may become available. Accordingly, in certain embodiments, the system can identify semi-direct medical device approaches based at least in part on a deformation of the approach region of an image. In some cases, the system can apply a flexibility factor to the approach region of the image. The flexibility factor can indicate a margin by which the approach region can be flexed. For example, the flexibility factor can indicate that the approach region can be flexed by 1-5 cm or by a percentage of the width or length of the image. Using the flexibility factor and other information as describe above, the system can identify one or more semi-direct medical device approaches.

Based on the identified medical device approaches the system can identify and display locations at the approach region for emplacing the medical device. In certain embodiments, the system can identify and display a particular emplacement for the medical device. For example, the system can highlight a region corresponding to the dimensions of the medical device. As another non-limiting example, based on two needle approach paths 216 determined to be acceptable, the system can display emplacements such as by displaying images of needles 218 along the acceptable paths 216, and/or by displaying highlighted or otherwise distinguishing portions of the approach region. Similarly, the system can display one or more ultrasound probe emplacements such as by displaying an image of an ultrasound probe 214, by displaying a scanning region or path 212, and/or by displaying a highlighted or otherwise distinguishable portion of the approach region.

In addition, in certain embodiments, the system can highlight the portions of the medical image area or volume that satisfy the density threshold and/or that can be used as part of a medical device approach. For example, the objects and/or voxels throughout the medical image area or volume that satisfy the density threshold can be highlighted, displayed in a particular color, or brought into focus. Similarly, the objects and/or voxels that do not satisfy the density threshold can be faded, taken out of focus, displayed in a different color etc.

In some embodiments, the system can track the location of a medical device and identify and display one or more medical device approaches based at least in part on the determined location of the medical device. The medical device approaches can be for the tracked medical device and/or for another medical device. For example, if the system is tracking a medical imaging device, it can display medical device approaches for the medical imaging device and/or for another medical device, such as an invasive medical device. In certain embodiments, the system can use the determined location of the medical device to display and/or highlight the medical device approaches that are nearest to the medical device. For example, if the system identifies six medical device approaches, it can use the determined location of the medical device to display or highlight the three medical device approaches that are closest to the determined location of the medical device.

Similar systems and methods can be applied with 3D volumetric images. FIG. 3 illustrates a 3D volumetric medical image 300 with exemplary image scanning and needle approach paths. The exemplary image 300 depicted in FIG. 3 includes a volume 302 containing a target structure 304, skin 306, bone 308, and other internal tissue 310. As described in greater detail with reference to FIG. 2, the system can determine approach paths, poses, and/or emplacements for medical devices such as an ultrasound probe 312 and a needle 314, or other medical device. In some aspects, acceptable, desirable, and/or suggested approach paths can be selected in a 3D volume based on the same or similar criteria as those discussed above with reference to FIG. 2. For example, ultrasound scanning paths can be selected so as to avoid regions of gas or bone 308 and/or based on imaging characteristics of the ultrasound probe 312. Needle approach paths can be selected so as to avoid regions of bone 308 or delicate structures, and/or based on the length of the needle 314.

Similar to the 2D system described with reference to FIG. 2, the system can use a variety of techniques to analyze and determine acceptable medical device approaches. For example, the system can utilize ray tracing, projective texture mapping, edge detection, one or more rendered images, etc., as described above by analyzing a plurality of direct or semi-direct paths between the approach region and the target structure 304. Some implementations can analyze the volume 302 along a plurality of spherical surfaces of increasing or decreasing radius, similar to the circular paths analyzed in 2D systems described above. Suggested emplacements 316 can then be displayed within the 3D volumetric medical image 300 for the reference of the physician.

When displaying 3D volumetric data, voxels in front (closer to the point-of-view location) can obscure the voxels behind them. In some instances, this can occlude information that can be important from preoperative 3D data. One way to address this is to allow the doctor to view the data as 2D slices 318, in cross section, etc., as described in greater detail in U.S. application Ser. No. 14/166,179, entitled, SYSTEMS, METHODS, APPARATUSES, AND COMPUTER-READABLE MEDIA FOR IMAGE MANAGEMENT IN IMAGE-GUIDED MEDICAL PROCEDURES, incorporated by reference herein in its entirety. For example, a 2D slice 318 can be displayed based on a location of a medical device such as an ultrasound probe 312, with the location of the probe 312 determined based on data received from one or more emplacement sensors.

Moreover, the determined location of the probe 312 can be used to select suggested emplacements for a second medical device. For example, where the emplacement data indicates the location of an ultrasound probe 312 imaging the target structure 304, the guidance system can select one or more needle emplacements 316 near the location of the probe 312 (e.g., to facilitate the physician's simultaneous manipulation of the probe 312 and needle 314). In some embodiments, a previously obtained, real-time, or near real-time medical image (e.g., an ultrasound image obtained from the probe 312) can be superimposed on the 2D slice 318. In some embodiments, to enhance the visibility of the 2D slice 318, the 2D slice 318 can be displayed with increased brightness relative to the surrounding 3D volumetric image 300, or the surrounding 3D volumetric image 300 can be displayed with partial transparency or out of focus.

Figure 4:
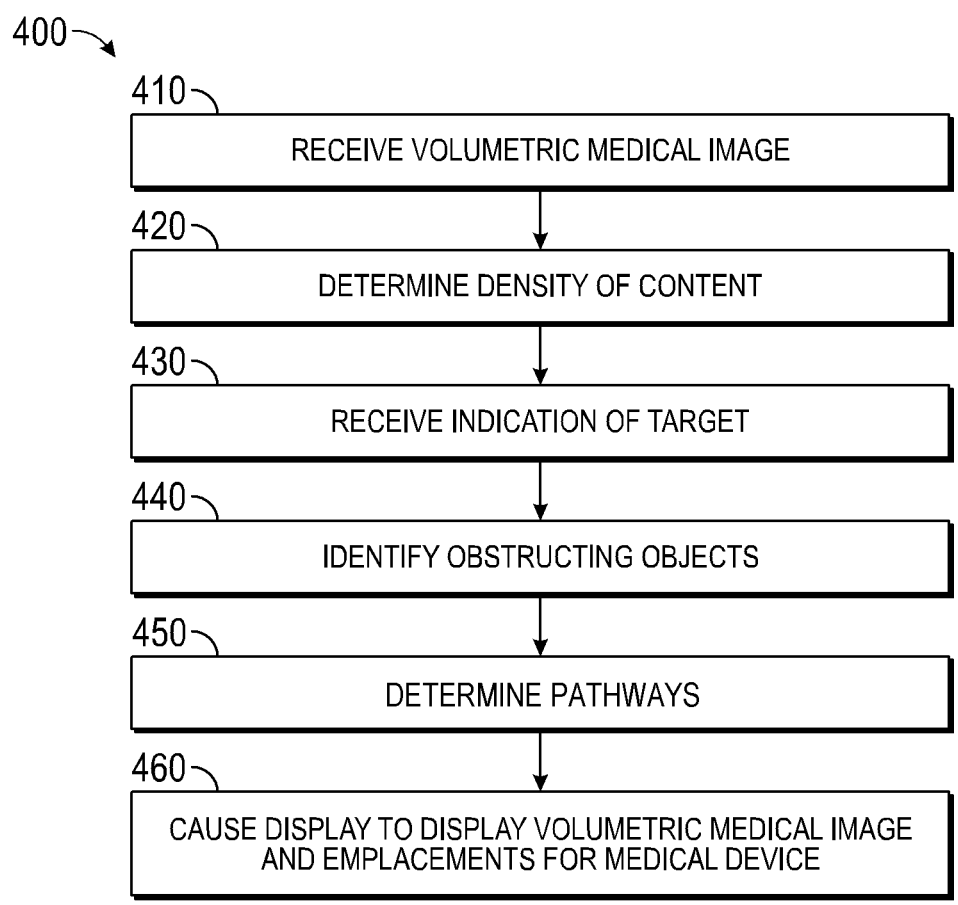
FIG. 4 is a flow diagram illustrative of an embodiment of a routine implemented by the system to display medical device emplacements.

FIG. 4 is a flow diagram illustrative of an embodiment of a routine 400 implemented to display medical device emplacements. One skilled in the relevant art will appreciate that the elements outlined for routine 400 can be implemented by one or more computing devices/components that are associated with the systems described herein. Further, it will be understood that the various blocks described herein with reference to FIG. 4 can be implemented in a variety of orders. For example, some blocks can be implemented concurrently or in a different order as desired. For example, the system can perform blocks 420 and 430 concurrently and/or implement them in a different order.

At block 410, a volumetric medical image is received. As described elsewhere herein, the volumetric medical image can be obtained from any of various medical imaging technologies, including without limitation ultrasound, CT scan, MRI, open-magnet MRI, optical coherence tomography, PET scans, fluoroscopy, ultrasound, or other preoperative or intraoperative 2D or 3D anatomical imaging data. The volumetric medical image can be received as a single set of 3D volumetric data, or can be received as a plurality of 2D slices as described with reference to FIGS. 1A-B. In some embodiments, a volumetric medical image received as a single set of 3D volumetric data can be converted into a plurality of 2D image slices, and/or a volumetric medical image received as a plurality of 2D slices can be converted to a 3D volume as desired.

At block 420, the density of content within the volumetric medical image can be determined. As described in greater detail above, in some embodiments, the density of content can be determined based at least in part on an intensity value of voxels associated with the content within the volumetric medical image. For example, the density of content can be determined using a Hounsfield unit scale or other suitable scale for determining a mass density based on an image intensity.

At block 430, an indication can be received of a target location within the volumetric medical image. As described in greater detail above, in some embodiments, the indication can be received from a human user, such as a physician, can be received based on an input by the user, such as a keystroke or button press, or the like, and/or can be determined by the system, for example, based on a computer analysis of a region within the medical image, a detected reaction of a user, an amount of time a medical device is located at a particular emplacement, etc. In another example, the target location can be determined based on a real-time medical image. For example, as depicted in FIG. 3, the target location can be determined based on a structure being scanned by a user with an ultrasound probe. The target location can be determined based on the combination of the location of the target structure within the real-time ultrasound image and the determined emplacement of the emplacement sensor associated with the ultrasound probe. In various embodiments, one or more target locations can be selected and/or stored.

At block 440, the system can identify one or more obstructing objects within the volumetric medical image. In some embodiments, the system can identify the obstructing objects based at least in part on the determined density of content within the volumetric medical image, or otherwise identified as not to be used for a medical device approach. In certain embodiments, obstructing objects can be determined based on regions within the volumetric medical image having a density that does not satisfy a density threshold. As described previously, the density threshold can be a minimum density, maximum density or range of densities. For example, the system can identify a region having a density approximately equal to the density of bone as an obstructing object.

In some embodiments, the density threshold can be based at least in part on one or more imaging characteristics of a medical imaging device. For example, the density threshold can be based at least in part on a scan frequency of the medical imaging device. The maximum density of objects through which waves and/or radiation emitted by a medical imaging device can pass can vary based on the frequency of the waves and/or radiation (e.g., a scan frequency). Thus, the density threshold can be determined based on the known scan frequency of the medical imaging device. In another example, the density threshold can be determined based on the type of medical device (e.g., whether the device is an intrusive device, medical imaging device, or other type of medical device). In some aspects, the density threshold can include a single threshold, or can include a range of densities. For example, a density threshold for an ultrasound imaging device can include the range between −350 HU and 700 HU, so as to exclude regions of intestinal gas, air, and bone.

At block 450, one or more pathways can be determined from an approach region of the volumetric medical image to the target location. In some embodiments, the pathways can be identified based on pathways from the approach region of the medical image to the target that do not intersect or pass through an obstructing object. In certain embodiments, the system can identify the pathways based on pathways from the approach region of the medical image to the target that intersect or pass through at least two image slices. The pathways can be determined based on the methods described elsewhere herein, such as ray tracing, projective texture mapping, one or more rendered images, analysis of circular paths, analysis of spherical surfaces, or other methods.

As described in greater detail above, in some implementations, the one or more pathways can be determined based at least in part on characteristics of the medical device, such as threshold quantity of transducing elements at a particular emplacement of a medical imaging device each having a direct path to the target location that does not pass through the identified obstructing objects, other imaging characteristics of the medical device, and/or physical characteristics of the medical device. For example, for an ultrasound probe having a plurality of detecting crystals disposed in a linear array with known spacing, the plurality of pathways can be selected to be wide enough that at least 1, 3, 5, 10, 15, or more crystals of the ultrasound probe will have a direct path to the target location clear of obstructing objects, or a certain percentage of the ultrasound probe's crystals will have a direct path to the target location.

As described previously, in some cases, the system can identify the one or more pathways based on a tracked location of a medical device. In certain embodiments, the pathways identified can be for the tracked medical device and/or for another medical device.

At block 460, the system can cause a display to concurrently display the volumetric medical image and a plurality of emplacements on the approach region of the volumetric medical image for emplacements of one or more medical devices. Emplacements can be determined based at least in part on the determined plurality of direct pathways. For example, an emplacement for a medical imaging device can be determined as a location along the approach region of the volumetric medical image where the image scanning path of the medical imaging device includes one of the determined plurality of direct pathways within the volumetric medical image. In some embodiments, the plurality of emplacements can be displayed based at least in part on a determined emplacement of an emplacement sensor based on emplacement data received from the emplacement sensor. For example, the emplacement sensor can be associated with a medical device such as an ultrasound probe.

In some embodiments, the system described herein can be implemented in conjunction with and/or as part of a guidance system, as described below with reference to FIGS. 5A, 5B, and as described in greater detail in U.S. application Ser. No. 15/199,630, filed concurrently herewith, entitled, LOUPE DISPLAY.

Figure 5A:
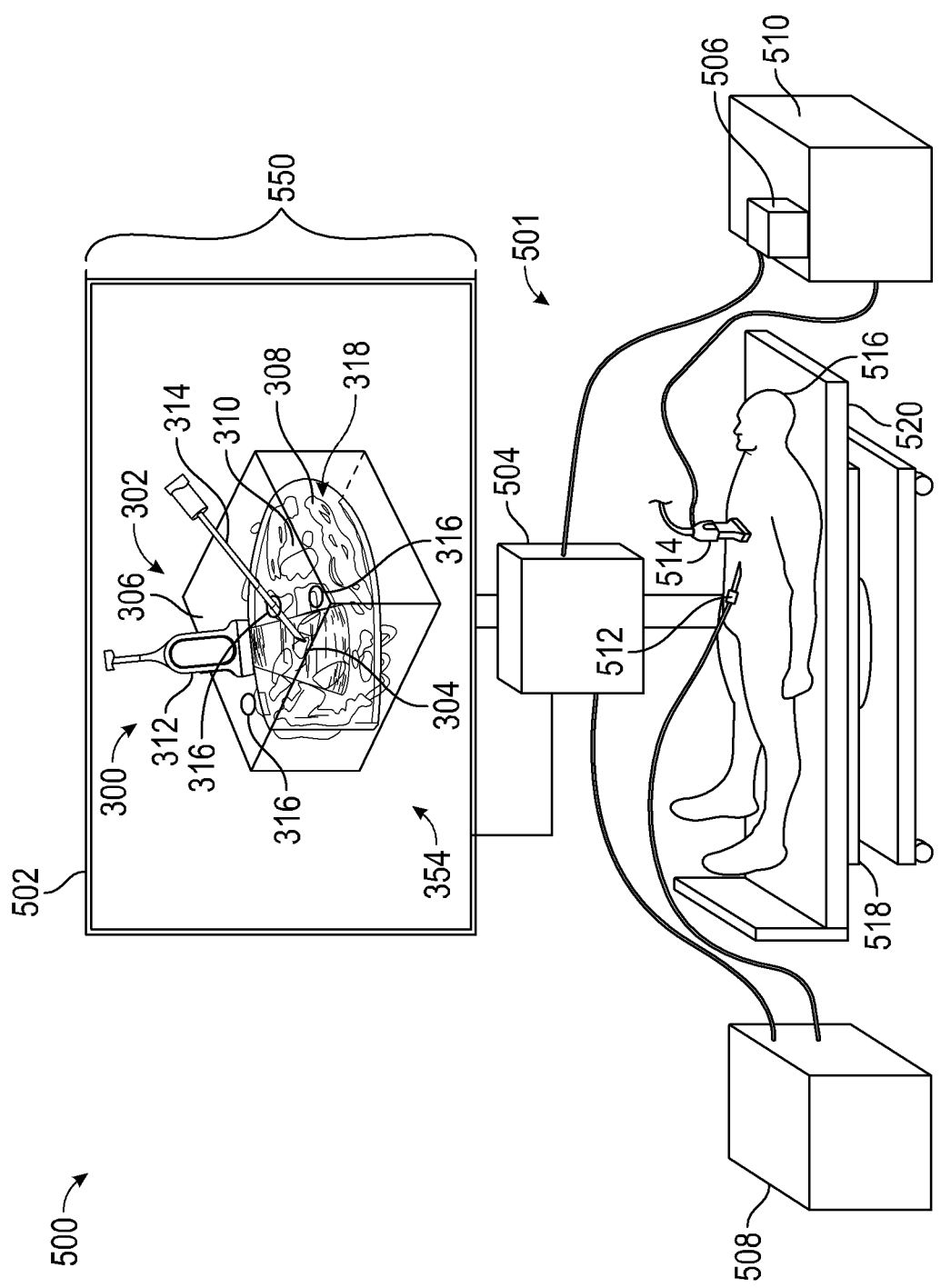
FIG. 5A is a diagram illustrating an embodiment of an environment for medical device approaches.

FIG. 5A is a diagram illustrating an embodiment of an environment 500 for image-guided medical device approaches. In the illustrated embodiment, the environment 500 includes a display 502 displaying an image 550, an image guidance unit 504, a position sensing unit 506, a surgical system 508, imager 510, medical devices 512, 514, a patient 516, a stand 518, and a table 520. In some embodiments, an image guidance system 501 can include any one or any combination of the display 502, the image guidance unit 504, the position sensing unit 506, the surgical system 508, the imager 510, the medical devices 512, 514, the stand 518, and/or the table 520.

In some embodiments, the position sensing unit 506 can track medical devices 512, 514 within an area or volume, which can also be referred to as a tracked region or position sensing region, and provide data to the image guidance unit 504.

Although only two medical devices 512, 514 are shown in FIG. 5A, it will be understood that additional medical devices can be tracked and associated data can be provided to the image guidance unit 504. The image guidance unit 504 can process or combine the data and show image guidance data on display 502. This image guidance data can be used by a healthcare provider to guide a procedure and improve care. The image guidance data can also be used by the system to identify the medical device approaches described above.

There are numerous other possible embodiments of system 501. For example, many of the depicted components can be joined together to form a single component and can be implemented in a single computer or machine. Further, additional position sensing units can be used in conjunction with position sensing unit 506 to track relevant medical devices 512, 514, as discussed in more detail below. Additional imagers 510 can be included, and combined imaging data from the multiple imagers 510 can be processed by image guidance unit 504 and shown on display 502. Additionally, two or more surgical systems 508 can be used.

Information about and from multiple surgical systems 508 and attached medical devices 512 (and additional medical devices not shown) can be processed by image guidance unit 504 and shown on display 502. These and other possible embodiments are discussed in more detail below. It will be understood that any combination of the display objects, image guidance cues, etc., described herein can be displayed concurrently, or simultaneously. Further, reference to displaying objects "concurrently" and/or "simultaneously" is to be interpreted broadly and may refer to displaying objects in such a way that to a human observer the objects are visible at the same time.

Imager 510 can be communicatively coupled to image guidance unit 504. In some embodiments, imager 510 can be coupled to a second display unit (not shown). The second display unit can display imaging data from imager 510. The imaging data displayed on display 502 and displayed on second display unit can be the same or different. In some embodiments, the imager 510 can be an ultrasound machine 510, the medical device 514 can be a movable imaging unit, such as an ultrasound transducer 514 or ultrasound probe 514, and the second display unit can be a display associated with the ultrasound machine 510 that displays the ultrasound images from the ultrasound machine 510. In some embodiments, a movable imaging unit 514 can be communicatively coupled to image guidance unit 504. The movable imaging unit 514 can be useful for allowing a user to indicate what portions of a first set of imaging data are to be displayed. For example, the movable imaging unit 514 can be an ultrasound transducer 514, a needle or other medical device, for example, and can be used by a user to indicate what portions of imaging data, such as an intraoperative or preoperative CT scan, to show on a display 502 as image 550. The movable imaging unit 514 can also be used to identify medical device approaches for the moveable imaging unit 514 and/or for the medical device 512. Further, in some embodiments, there can be a third set of intraoperative or preoperative imaging data that can be displayed with the first set of imaging data.

In some embodiments, a navigation system 501 comprises a display 502 and a position sensing unit 506 communicatively coupled to image guidance unit 504. In some embodiments, position sensing unit 506, display 502, and image guidance unit 504 are coupled to the stand 518. Image guidance unit 504 can be used to produce images 550 that are displayed on display 502. The images 550 produced on display 502 by the image guidance unit 504 can be determined based on ultrasound or other visual images from the first medical device 512 and second medical device 514.

In the illustrated embodiment, the image 550 can include the volumetric medical image 300 described above in greater detail. In the image 550, some or all of the display objects can be displayed as 3D objects. Furthermore, the display objects in the image 550 can be displayed in a perspective based at least in part on a point-of-view location. More medical devices can be added to the system 501 as desired. For example, the system 501 can include an ultrasound probe, ablation needle, laparoscopic camera, stapler, cauterizer, scalpel and/or any other medical device or medical device, and the system 501 can determine a medical device approach for any one or more of the medical devices. The system 501 can also process and/or display collected data, such as preoperative CT scans, X-Rays, MRIs, laser scanned 3D surfaces etc.

In some embodiments, the imaging data obtained from one or both of medical devices 512 and 514 can include other modalities such as a CT scan, MRI, open-magnet MRI, optical coherence tomography ("OCT"), positron emission tomography ("PET") scans, fluoroscopy, ultrasound, or other preoperative, or intraoperative 6D or 3D anatomical imaging data. In some embodiments, medical devices 512 and 514 can also be scalpels, implantable hardware, or any other device used in surgery. Any appropriate surgical system 508 or imager 510 can be communicatively coupled to the corresponding medical instruments 512 and 514.

The medical devices 512, 514 can be communicatively coupled to the position sensing unit 506 (non-limiting example: sensors embedded or coupled to the medical devices 512, 514 can be communicatively coupled with the position sensing unit 506). The position sensing unit 506 can be part of imager 510 or it can be separate. The position sensing unit 506 can be used to determine the emplacement of first medical device 512 and/or the second medical device 514. In some embodiments, the position sensing unit 506 can include a magnetic tracker and/or one or more magnetic coils can be coupled to medical devices 512 and/or 514. In some embodiments, the position sensing unit 506 can include an optical tracker and/or one or more visually-detectable fiducials can be coupled to medical devices 512 and/or 514. In some embodiments, the position sensing unit 506 can be located below the patient. In such embodiments, the position sensing unit 506 can be located on or below the table 520. For example, in embodiments where the position sensing unit 506 is a magnetic tracker, it can be mounted below the surgical table 520. Such an arrangement can be useful when the tracking volume of the position sensing unit 506 is dependent on the location of the position sensing unit 506, as with many magnetic trackers. In some embodiments, magnetic tracking coils can be mounted in or on the medical devices 512 and 514.

In some embodiments, the position sensing unit can determine one or more x, y, z coordinates and/or the quaternions (non-limiting examples: yaw, pitch, and/or roll) of tracking sensors associated with one or more of the medical devices 512, 514. In certain cases, the position sensing unit can determine the one or more x, y, z coordinates of the tracking sensors with respect to a position sensing coordinate system, as described in greater detail below. In some embodiments, the position sensing unit 506 can be an electromagnetic measurement system (non-limiting example: NDI Aurora system) using sensor coils for tracking sensors attached to the first and/or second medical devices 512, 514. In some embodiments, the position sensing unit 506 can be an optical 3D tracking system using fiducials for tracking sensors. Such optical 3D tracking systems can include the NIDI Polaris Spectra, Vicra, Certus, PhaseSpace IMPULSE, Vicon MX, InterSense IS-900, NaturalPoint OptiTrack, Polhemus FastTrak, IsoTrak, or Claron MicronTracker2. In some embodiments, the position sensing unit 506 can each be an inertial 3D tracking system comprising a compass, accelerometer, tilt sensor, and/or gyro, such as the InterSense InertiaCube or the Nintendo Wii controller, mechanical tracking system, camera-based tracking system, radar-based tracking system, etc. In some embodiments, the position sensing unit 506 can be attached to or affixed on the corresponding medical device 512 and 514.

In some embodiments, the position sensing units 506, can include sensing devices such as the HiBall tracking system, a GPS device, or signal emitting device that would allow for tracking of the position and/or orientation (non-limiting example: emplacement) of the tracking sensor (also referred to as an emplacement sensor). In some embodiments, a position sensing unit 506 can be affixed to either or both of the medical devices 512, 514. The medical devices 512 or 514 can be tracked by the position sensing unit 506. A room coordinate system reference, such as the display 502 can also be tracked by the position sensing unit 506 in order to determine the emplacements of the medical devices 512, 514 with respect to the room coordinate system. Devices 512, 514 can also include or have coupled thereto one or more accelerometers, which can be used to estimate movement, position, and location of the devices. In some embodiments, the position sensing unit 506 can be an Ascension Flock of Birds, Nest of Birds, driveBAY, medSAFE, trakSTAR, miniBIRD, MotionSTAR, pciBIRD, or Calypso 6D Localization System and tracking sensors attached to the first and/or second medical devices 512, 514 can be magnetic tracking coils.

The term "tracking sensor" (also referred to as an emplacement sensor), as used herein, is a broad term encompassing its plain and ordinary meaning and includes without limitation all types of magnetic coils or other magnetic field sensing devices for use with magnetic trackers, fiducials or other optically detectable markers for use with optical trackers, such as those discussed above and below, or other sensors, such as accelerometers, gyroscopes, etc. In some embodiments, the tracking sensors can be implemented using optical position sensing devices, such as the HiBall tracking system and the position sensing unit 506 can form part of the HiBall tracking system. Tracking sensors can also include a GPS device or signal emitting device that allows for tracking of the position and/or orientation of the tracking sensor. In some embodiments, a signal emitting device might include a radio-frequency identifier (RFID). In such embodiments, the position sensing unit 506 can use the GPS coordinates of the tracking sensors or can, for example, triangulate the radio frequency signal being emitted by the RFID associated with tracking sensors. The tracking systems can also include one or more 3D mice.

In certain embodiments, the system 501 can register the location of the volumetric medical image 300 to the position sensing region and/or the patient 516. Accordingly, the system 501 can use the emplacement data and registered volumetric medical image 300 to identify the location of the medical devices 512, 514, relative to the volumetric medical image 300, as well as identify the emplacement of the medical devices 512, 514 relative to the identified medical device approaches.

Furthermore, the system 501 can use the emplacement data associated with the tracking sensors (non-limiting example: received from the tracking sensors or from the position sensing unit 506) to determine other emplacement information, including, but not limited to the emplacement of the medical device approaches as described above. In some cases, the tracking sensors can output the emplacement data, which can be used by the tracker to determine the emplacement of the tracking sensor. In certain cases, the tracker tracking the tracker sensors determines the emplacement of the tracking sensors without data being output from the tracking sensors.

In some embodiments, the display 502 displays 3D images to a user, such as a healthcare provider. Stereoscopic 3D displays separate the imagery shown to each of the user's eyes. This can be accomplished by a stereoscopic display, a lenticular auto-stereoscopic display, or any other appropriate type of display. The display 502 can be an alternating row or alternating column display. Example alternating row displays include the Miracube G240S, as well as Zalman Trimon Monitors. Alternating column displays include devices manufactured by Sharp, as well as many "auto-stereoscopic" displays (non-limiting example: Philips). In some embodiments, Sony Panasonic 3D passive displays and LG, Samsung, and/or Vizio 3D TVs can be used as well. Display 502 can also be a cathode ray tube. Cathode Ray Tube (CRT) based devices, can use temporal sequencing, showing imagery for the left and right eye in temporal sequential alternation. This method can also be used by projection-based devices, as well as by liquid crystal display (LCD) devices, light emitting diode (LED) devices, organic LED (OLED) devices, liquid crystal on silicon (LCOS) devices, DLP devices, virtual retinal display (MicroVision) devices, or the like.

In certain embodiments, the display 502 can be a head mounted display (HMD) worn by the user in order to receive 3D images from the image guidance unit 504. In such embodiments, a separate display, such as the pictured display 502, can be omitted. The 3D graphics can be produced using underlying data models, stored in the image guidance unit 504 and projected onto one or more 6D planes in order to create left and right eye images for a head mount, lenticular, or other 3D display.

The underlying 3D model can be updated based on the relative emplacements of the various devices 512 and 514, as determined by the position sensing unit(s) 506, and/or based on new data associated with the devices 512 and 514. For example, if the second medical device 514 is an ultrasound probe, then the underlying data model can be updated to reflect the most recent ultrasound image. If the first medical device 512 is an ablation needle, then the underlying model can be updated to reflect any changes related to the needle, such as power or duration information.

Any appropriate 3D graphics processing can be used for rendering including processing based on OpenGL, Direct3D, Java 3D, etc. Whole, partial, or modified 3D graphics packages can also be used, such packages including 3DS Max, SolidWorks, Maya, Form Z, Cybermotion 3D, VTK, Slicer, or any others. In some embodiments, various parts of the needed rendering can occur on traditional or specialized graphics hardware. The rendering can also occur on the general CPU, on programmable hardware, on a separate processor, be distributed over multiple processors, over multiple dedicated graphics cards, or using any other appropriate combination of hardware or technique.

One or more components, units, devices, or elements of various embodiments can be packaged and/or distributed as part of a kit. For example, in one embodiment, an ablation needle, one or more tracking sensors, 3D viewing glasses, and/or a portion of an ultrasound wand can form a kit. Other embodiments can have different elements or combinations of elements grouped and/or packaged together. Kits can be sold or distributed separately from or with the other portions of the system 501.

One will readily recognize that there are numerous other examples of image guidance systems 501 which can use, incorporate, support, or provide for the techniques, methods, processes, and systems described herein.

With continued reference to FIG. 5A, the display 502 shows a perspective view of the volumetric medical image 300, a virtual ultrasound probe 316, and a virtual needle 314. The virtual medical devices 314, 316 can be displayed in a virtual 3D scene with the display 502 acting as a window into the virtual 3D scene. Thus, as a medical device 512 is moved to the right with respect to a point-of-view location (non-limiting example: the location of the point-of-view for viewing the 3D space), the virtual medical device 558 can also move to the right. In some embodiments, the virtual medical devices 314, 316 can correspond to determined medical device emplacements for the medical devices 512, 514. For example, the virtual medical devices 314, 316 can indicate where the medical devices 512, 514 are to be emplaced. In such embodiments, the display 502 can include additional virtual medical devices indicating the determined location of the medical devices 512, 514 relative to the recommended emplacements. Additional cues can be displayed to aid the user in emplacing the medical devices in the recommended emplacements.

In some embodiments, if the medical device 512 is rotated 90° so that the tip of the medical device is pointing away from the point-of-view location (non-limiting example: at the display 502), the virtual medical device 558 will likewise show the change in orientation, and show the tip of the virtual medical device 558 in the background and the other end of the virtual medical device 558 in the foreground. In some embodiments, as described in greater detail in U.S. application Ser. No. 14/212,933, incorporated herein by reference in its entirety, the point-of-view location can be a fixed location, such as a predetermined distance/angle from the display 502 or stand 518 and or a location configured by the user; or the point-of-view location can by dynamic. For example, the system 501 can track a user in real-time and determine the point-of-view location based at least in part on the tracked location of the user.

Other embodiments can track and display other types of instruments and their features. For example, a healthcare provider may want to track one or more of a scalpel, a biopsy, a cauterizer (including an electrocauterizer and Bovies), forceps, cutting loops on hysteroscopes, harmonic shears, lasers (including $CO_2$ lasers), etc. For example, in various embodiments, the following devices can be tracked and various aspects of their design displayed on display 502: Olympus™ OES Pro Hystero-Resectoscope, SonoSurg Ultrasonic Surgical System Olympus™ GF-UC 560 Endoscope Wallus™ Embryo Transfer Catheter AngioDynamics® NanoKnife™, VenaCure™ laser, StarBurst, Uniblade, Habib® Resector Bovie™ Electrodes, Covidien Evident™, Cool-Tip™ Ablation Antennas, Opti4™ Electrodes Microsulis MEA (microwave endometrial ablation), Acculis Halt™ Medical System Optimed BigLumen Aspiration Catheter Optimed Optipure Stent Central venous catheterization introducer medical device (such as those made by Bard and Arrow).

Once tracked, a healthcare provider is able to see image guidance data on display 502 that will allow her to know the relative pose, location, or emplacement of the tracked instrument(s) with respect to one another or with respect to imaging data and will be able to see, on display 620, the features of the instrument rendered in the scene.

Figure 5B:
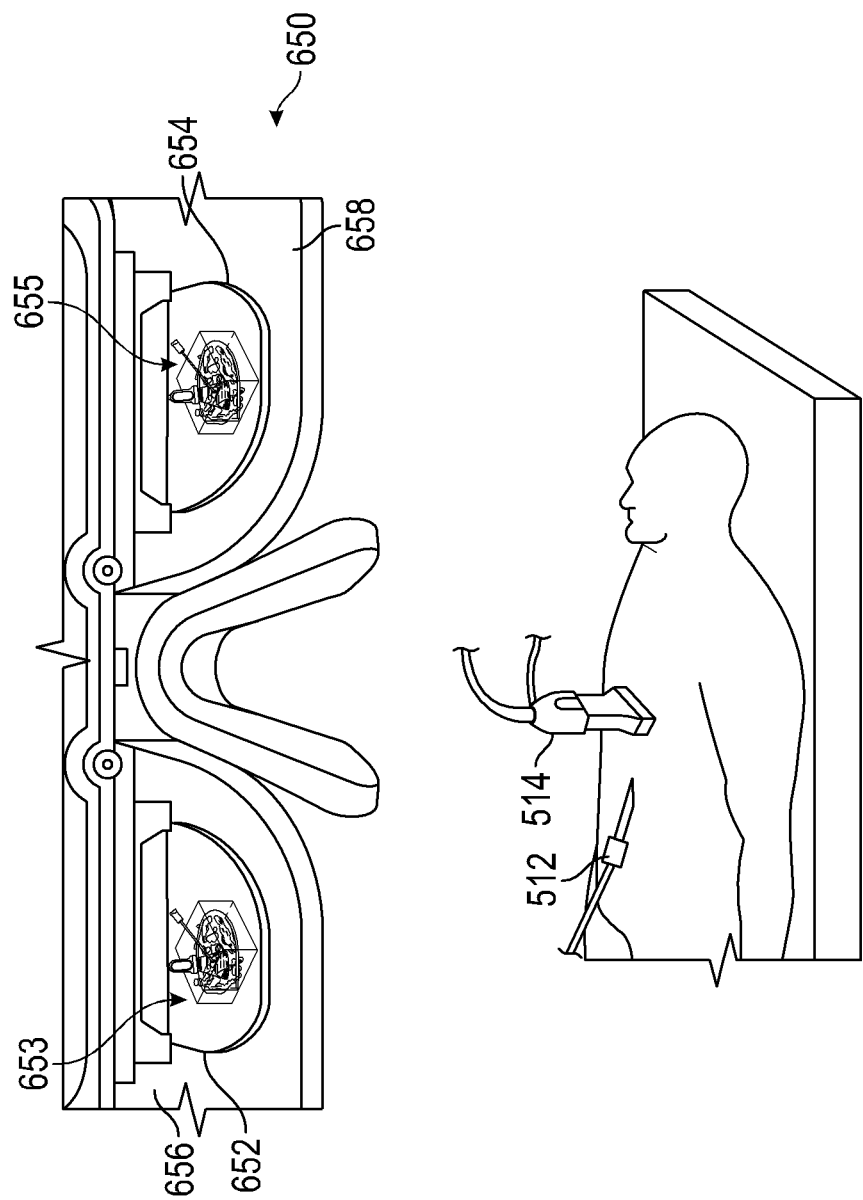
FIG. 5B is a diagram illustrating an embodiment of a rendering of medical device approaches on a head mounted display.

Referring now to FIG. 5B, virtual image content may be displayed on a head mounted display (HMD) 650 instead of or in addition to a display 502 as depicted in FIG. 5A. The HMD 650 may include one or more stereoscopic displays 652, 654 configured to display 3D content to a wearer of the HMD 650. For example, the HMD 650 can include a left stereoscopic display 652 configured to project visual content 653 to a left eye of a wearer, and a right stereoscopic display 654 configured to display visual content 655 to a right eye of a wearer. In some embodiments, displays 652, 654 can be opaque, and can be sized and located so as to occupy a subset of the field of view of a wearer. In certain embodiments, the displays 652, 654 can be transparent or translucent, or can be implemented as retinal scan displays that project an image onto the eye rather than display an image on the display screen.

Displays 652, 654 can allow the displayed content 653, 655 to be seen clearly without glare or interference due to light from the world in the region beyond the displays 652, 654. In certain embodiments, displays 652, 654 occupying less than the entire field of view of the wearer can allow the wearer to view the virtual content 653, 655 while also viewing the real environment in the portion of the wearer's field of view unoccupied by displays 652, 654, such as through transparent portions 656, 658 of the HMD 650.

In some embodiments, the imaging systems described herein can display virtual image content on the displays 652, 654 using a location offset with respect to the location of corresponding objects. For example, rather than displaying and/or augmenting content that is directly in front of the displays 652, 654 and/or the HMD 650, the displays 652, 654 can display and/or augment objects that are located elsewhere, such as below, above, or to the side of the displays 652, 654 and/or the HMD 650. In the illustrated embodiment, the virtual medical devices 314, 316 can be displayed with a vertical offset relative to the medical devices 512, 514 so as to allow a wearer of the HMD 650, such as a surgeon, to simultaneously view the virtual medical devices 558, 560 on the displays 652, 654 and the patient 516 with real medical devices 512, 514 located below the HMD 650.

The offset can be predetermined based on a dimension or preference of an individual wearer prior to use, or based on a default such as an average height or dimension of an expected wearer, or dynamic based on data received during use. An example offset can be a distance equal or approximately equal to the vertical distance between a wearer's elbow and the wearer's eye (non-limiting example: in the range of 0.5 m to 5 m), a measured distance between the HMD 650 and the medical devices 512, 514, etc. Additional details regarding the offset are described in U.S. application Ser. No. 15/199,630, filed concurrently herewith, entitled, LOUPE DISPLAY.

The HMD 650 can be implemented with any of the imaging systems described with reference to FIG. 5A. For example, displays 652, 654 can display virtual medical devices 558, 560 corresponding to real medical devices 512, 514. Displays 652, 654 can further display any other virtual image features described elsewhere herein, such as a medical device approach.

The processes, computer readable medium, and systems described herein can be performed on various types of hardware, such as computer systems or computing devices. In some embodiments, position sensing units, a display unit, image guidance units, and/or any other module or unit of embodiments herein can each be separate computing devices, applications, or processes or can run as part of the same computing devices, applications, or processes—or one of more can be combined to run as part of one application or process—and/or each or one or more can be part of or run on a computing device. Computing devices or computer systems can include a bus or other communication mechanism for communicating information, and a processor coupled with the bus for processing information. A computer system or device can have a main memory, such as a random access memory or other dynamic storage device, coupled to the bus. The main memory can be used to store instructions and temporary variables. The computer system or device can also include a read-only memory or other static storage device coupled to the bus for storing static information and instructions. The computer systems or devices can also be coupled to a display, such as a CRT, LCD monitor, LED array, e-paper, projector, or stereoscopic display. Input devices can also be coupled to the computer system or device. These input devices can include a mouse, a trackball, touchscreen, tablet, foot pedal, or cursor direction keys.

Each computer system or computing device can be implemented using one or more physical computers, processors, embedded devices, field programmable gate arrays (FPGAs), or computer systems or portions thereof. The instructions executed by the computer system or computing device can also be read from a computer-readable medium. The computer-readable medium can be non-transitory, such as a CD, DVD, optical or magnetic disk, laserdisc, flash memory, or any other medium that is readable by the computer system or device. In some embodiments, hardwired circuitry can be used in place of or in combination with software instructions executed by the processor. Communication among modules, systems, devices, and elements can be over a direct or switched connections, and wired or wireless networks or connections, via directly connected wires, or any other appropriate communication mechanism. Transmission of information can be performed on the hardware layer using any appropriate system, device, or protocol, including those related to or utilizing Firewire, PCI, PCI express, CardBus, USB, CAN, SCSI, IDA, RS232, RS422, RS485, 802.11, etc. The communication among modules, systems, devices, and elements can include handshaking, notifications, coordination, encapsulation, encryption, headers, such as routing or error detecting headers, or any other appropriate communication protocol or attribute. Communication can also messages related to HTTP, HTTPS, FTP, TCP, IP, ebMS OASIS/ebXML, DICOM, DICOS, secure sockets, VPN, encrypted or unencrypted pipes, MIME, SMTP, MIME Multipart/Related Content-type, SQL, etc.

Any appropriate 3D graphics processing can be used for displaying or rendering, including processing based on OpenGL, Direct3D, Java 3D, etc. Whole, partial, or modified 3D graphics packages can also be used, such packages including 3DS Max, SolidWorks, Maya, Form Z, Cybermotion 3D, VTK, Slicer, or any others. In some embodiments, various parts of the needed rendering can occur on traditional or specialized graphics hardware. The rendering can also occur on the general CPU, on programmable hardware, on a separate processor, be distributed over multiple processors, over multiple dedicated graphics cards, or using any other appropriate combination of hardware or technique.

As will be apparent, the features and attributes of the specific embodiments disclosed above can be combined in different ways to form additional embodiments, all of which fall within the scope of the present disclosure.

Conditional language used herein, such as, among others, "can," "could," "might," "can," "e.g.,," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Any process descriptions, elements, or blocks in the processes, methods, and flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions can be deleted, executed out of order from that shown or discussed, including substantially concurrently or in reverse order, depending on the functionality involved, as would be understood by those skilled in the art.

All of the methods and processes described above can be embodied in, and fully automated via, software code modules executed by one or more general purpose computers or processors, such as those computer systems described above. The code modules can be stored in any type of computer-readable medium or other computer storage device. Some or all of the methods can alternatively be embodied in specialized computer hardware.

It should be emphasized that many variations and modifications can be made to the above-described embodiments, the elements of which are to be understood as being among other acceptable examples. All such modifications and variations are intended to be included herein within the scope of this disclosure and protected by the following claims.

What is claimed is:

1. A method of medical imaging device guidance, the method comprising:
   receiving a volumetric medical image, the volumetric medical image including a plurality of image slices;
   determining a density of content within the volumetric medical image based at least in part on an intensity value of voxels associated with the content within the volumetric medical image;
   receiving an indication of a target location within the volumetric medical image;
   identifying based at least in part on the determined density of the content obstructing objects within the volumetric medical image having a density that does not satisfy a density threshold, wherein the density threshold is based at least in part on one or more imaging characteristics of a medical imaging device;
   determining a plurality of direct pathways from an approach region of the volumetric medical image to the target location that pass through at least two of the plurality of image slices and that do not pass through the obstructing objects; and
   causing a display to concurrently display:
   the volumetric medical image, and
   a plurality of emplacements on the approach region of the volumetric medical image for emplacement of the medical imaging device based at least in part on the determined plurality of direct pathways.

2. The method of claim 1, further comprising:
   receiving emplacement data associated with an emplacement sensor; and
   further causing the display to concurrently display the plurality of emplacements on the approach region of the volumetric medical image for emplacement of the medical imaging device based at least in part on the emplacement data.

3. The method of claim 1, wherein the imaging characteristics of the medical imaging device comprise a scan frequency of the medical imaging device and wherein the density threshold is based at least in part on scan frequency.

4. The method of claim 3, wherein said determining a plurality of direct pathways from an approach region of the volumetric medical image to the target location is further based at least in part on a threshold quantity of transducing elements at a particular emplacement of the medical imaging device each having a direct path to the target location that does not pass through the obstructing objects.

5. A method of medical device guidance, the method comprising:
   determining a density of content within a volumetric medical image based at least in part on an intensity value of voxels associated with the content within the volumetric medical image;
   receiving an indication of a target location within the volumetric medical image;
   identifying, based at least in part on the determined density of the content, obstructing objects within the volumetric medical image having a density that does not satisfy a density threshold, wherein the density threshold is based at least in part on one or more characteristics of a medical device;
   determining a plurality of pathways from an approach region of the volumetric medical image to the target location that do not pass through the obstructing objects; and
   causing a display to concurrently display:
      the volumetric medical image, and
      a plurality of emplacements on the approach region of the volumetric medical image for emplacement of the medical device based at least in part on the determined plurality of pathways.

6. The method of claim 5, wherein the medical device is a first medical device, the method further comprising:
   receiving emplacement data associated with an emplacement sensor, the emplacement sensor associated with a second medical device; and
   further causing the display to concurrently display the plurality of emplacements on the approach region of the volumetric medical image for emplacement of the first medical device based at least in part on the emplacement data.

7. The method of claim 6, wherein said receiving an indication of the target location within the volumetric medical image is based at least in part on the determined emplacement of the emplacement sensor.

8. The method of claim 6, wherein said determining the plurality of pathways from the approach region of the volumetric medical image to the target location is based at least in part on the determined emplacement of the emplacement sensor and one or more dimensions of the first medical device.

9. The method of claim 5, wherein the characteristics of the medical device comprise a type of the medical device.

10. The method of claim 9, wherein the type of medical device is a medical imaging device and the density threshold is further based at least in part on a scan frequency of the medical imaging device.

11. The method of claim 10, wherein said determining a plurality of pathways from an approach region of the volumetric medical image to the target location is further based at least in part on a threshold quantity of transducing elements of the medical imaging device at a particular emplacement of the medical imaging device each having a direct path to the target location that does not pass through the obstructing objects.

12. The method of claim 10, wherein said determining a plurality of pathways from an approach region of the volumetric medical image to the target location is further based at least in part on a scan depth of the medical imaging device.

13. The method of claim 9, wherein the type of medical device is an invasive medical device, wherein said determining the plurality of pathways from the approach region of the volumetric medical image to the target location is further based at least in part on at least one of a length of the invasive medical device or a width of the invasive medical device.

14. The method of claim 5, wherein the volumetric medical image is a first volumetric medical image corresponding to a first time during a breathing cycle of a patient, the obstructing objects are first obstructing objects and the plurality of pathways is a first plurality of pathways, the method further comprising:
   identifying second obstructing objects within a second volumetric medical image having a density that does not satisfy the density threshold, the second volumetric medical image corresponding to a second time during the breathing cycle; and
   determining a second plurality of pathways from an approach region of the second volumetric medical image to the target location that do not pass through the second obstructing objects.

15. The method of claim 5, further comprising determining a plurality of semi-direct pathways from the approach region of the volumetric medical image to the target location that do not pass through the obstructing objects based at least in part on a deformation of the approach region of the volumetric medical image.

16. The method of claim 5, wherein said receiving the indication of the target location within the volumetric medical image is based at least in part on an amount of time that a medical device is located at a particular location.

17. The method of claim 5, wherein the density threshold comprises a range of densities.

18. The method of claim 5, wherein said determining the plurality of pathways from an approach region of the volumetric medical image to the target location that do not pass through the obstructing objects comprises:
   capturing a volume of voxels between the target to the approach region;
   mapping the volume of voxels to an image area; and
   identifying at least a portion of the image in which the approach region is visible.

* * * * *